(12) United States Patent
Bauer et al.

(10) Patent No.: US 12,030,855 B2
(45) Date of Patent: *Jul. 9, 2024

(54) PROCESS FOR MAKING AMINO DIARYL ETHERS AND AMINO DIARYL ETHERS HYDROCHLORIDE SALTS

(71) Applicant: CELLESTIA BIOTECH AG, Basel (CH)

(72) Inventors: Michael Bauer, Basel (CH); Uwe Hahn, Basel (CH); Erhard Bappert, Basel (CH)

(73) Assignee: Cellestia Biotech AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/882,432

(22) Filed: Aug. 5, 2022

(65) Prior Publication Data

US 2022/0388961 A1 Dec. 8, 2022

Related U.S. Application Data

(63) Continuation of application No. 17/254,166, filed as application No. PCT/EP2019/066381 on Jun. 20, 2019, now Pat. No. 11,472,771.

(30) Foreign Application Priority Data

Jun. 21, 2018 (EP) .................... 18179034.6

(51) Int. Cl.
| | | |
|---|---|---|
| C07D 213/62 | (2006.01) | |
| A61K 31/44 | (2006.01) | |
| A61P 35/00 | (2006.01) | |
| C07D 213/61 | (2006.01) | |

(52) U.S. Cl.
CPC ............ C07D 213/62 (2013.01); A61K 31/44 (2013.01); A61P 35/00 (2018.01); C07D 213/61 (2013.01); C07B 2200/13 (2013.01)

(58) Field of Classification Search
CPC ..... C07D 213/62; C07D 213/61; A61P 35/00; A61K 31/44; C07B 2200/13
See application file for complete search history.

(56) References Cited

U.S. PATENT DOCUMENTS

| | | | |
|---|---|---|---|
| 4,816,373 A | 3/1989 | Ohashi et al. | |
| 4,935,465 A | 6/1990 | Garman | |
| 5,780,482 A | 7/1998 | Armitage et al. | |
| 5,965,740 A | 10/1999 | Kai et al. | |
| 6,342,244 B1 | 1/2002 | Zalipsky | |
| 6,692,919 B1 | 2/2004 | Artavanis Tsakonas et al. | |
| 9,296,682 B2 * | 3/2016 | Radtke ............... | G01N 33/6872 |
| 10,054,581 B1 | 8/2018 | Radtke et al. | |
| 11,472,771 B2 * | 10/2022 | Bauer ............... | C07D 213/62 |
| 2003/0176438 A1 | 9/2003 | Arienti et al. | |
| 2005/0101521 A1 | 5/2005 | Miyachi et al. | |
| 2005/0171328 A1 | 8/2005 | Harris | |
| 2006/0002924 A1 | 1/2006 | Bodmer et al. | |
| 2006/0074024 A1 | 4/2006 | Bunting et al. | |
| 2007/0265264 A1 | 11/2007 | Battista et al. | |
| 2008/0161366 A1 | 7/2008 | McComas et al. | |
| 2008/0269265 A1 | 10/2008 | Miller et al. | |
| 2009/0081238 A1 | 3/2009 | Siebel et al. | |
| 2009/0105266 A1 | 4/2009 | Glatthar et al. | |
| 2010/0120869 A1 | 5/2010 | Ajioka et al. | |
| 2010/0234463 A1 | 9/2010 | Churcher et al. | |
| 2010/0292193 A1 | 11/2010 | McBride et al. | |
| 2012/0202785 A1 | 8/2012 | Heald et al. | |
| 2015/0246938 A1 | 9/2015 | Matsumura et al. | |

FOREIGN PATENT DOCUMENTS

| | | |
|---|---|---|
| EP | 1820795 A1 | 8/2007 |
| JP | 2001089412 A | 4/2001 |
| WO | WO 93/25225 A1 | 12/1993 |
| WO | WO 98/41525 A1 | 9/1998 |
| WO | WO 00/42012 A1 | 7/2000 |
| WO | WO 2003/051825 A1 | 6/2003 |
| WO | WO 2005/047366 A1 | 5/2005 |
| WO | WO 2006/020951 A1 | 2/2006 |
| WO | WO 2009/060209 A1 | 5/2009 |
| WO | WO 2009/146875 A1 | 12/2009 |
| WO | WO 2010/033655 A1 | 3/2010 |
| WO | WO 2013/093885 A1 | 6/2013 |

OTHER PUBLICATIONS

Bharate, S. S. "Recent Developments in Pharmaceutical Salts: FDA Approvals from 2015 to 2019." Drug Discover Today, vol. 26, No. 2, Feb. 2021, pp. 384-398.

Clinton, R. 0 et al. "A Structure Proof for 4-(4-Diethylamino-1-methylbutylamino)-7 phenoxyquinoline." Journal of the American Chemical Society, vol. 69, No. 3, Mar. 1, 1947, pp. 704 706.

King, H. "254. Curare Alkaloids. Part IV. Bebeerine and Tubocurarine. Orientation of Phenolic Groups." Journal of the Chemical Society, 1939, pp. 1157-1164.

Krug, M. et al. "Discovery and Selectivity-profiling of 4-benzylamino 1-aza-9-oxafluorene Derivatives as Lead Structures for IGF-1R Inhibitors." Bioorganic & Medicinal Chemistry Letters, vol. 20, No. 23, Dec. 1, 2010, pp. 6915-6919.

(Continued)

*Primary Examiner* — Timothy R Rozof

(74) *Attorney, Agent, or Firm* — Fenwick & West LLP; Hayan Yoon; Cara A. Mosley

(57) ABSTRACT

The present invention relates to a process for making a compound of formula (I) as described herein Formula (I) comprising reducing a compound of formula (II) as described herein with hydrogen in the presence of a palladium catalyst and a solvent wherein the solvent is a polar, aprotic solvent or a C3-C10 alcohol Formula (II). The present invention further relates to a hydrochloride salt and a monohydrochloride salt of the compound of formula (I) as described herein and to a process for making the same Formula (I).

22 Claims, 6 Drawing Sheets

(56) References Cited

OTHER PUBLICATIONS

Lange, N. A. et al. "Some Para-Phenoxy-Ureas and Thio-Ureas Derived from Para-Phenoxy-Aniline. The Effect of the Phenoxy Group on the Taste." Journal of the American Chemical Society, vol. 48, No. 4, Apr. 1, 1926, pp. 1069-1074.
PCT International Search Report and Written Opinion, PCT Application No. PCT/EP2019/066381, dated Nov. 19, 2019, 17 pages.
Stahl, P.H. et al. "Appendix." Handbook of Pharmaceutical Salts: Properties, Selection, and Use, Wiley-VCH, 2002, pp. 329-331.
Szajnman, S. H. et al. "Design and Synthesis of Aryloxyethyl Thiocyanate Derivatives as Potent Inhibitors of Trypanosoma cruzi Proliferation." Journal of Medical Chemistry, vol. 43, No. 9, Apr. 14, 2000, pp. 1826-1840.
Udeh, C. U. et al. "Tuning Structure and Function in Tetra(aniline)-based rod-coil-rod Architectures." Journal of Materials Chemistry C, vol. 1, No. 39, Aug. 30, 2013, DD. 6428-6437.
3-Pyridinamine, 6-[3-(1,1-dimethylethyl)phenoxy]-, Feb. 1, 2009, CAS Registry No. 1098366-43-8 (3 pages).
3-Pyridinamine, 6-[4-(1,1-dimethylpropyl)phenoxy]-, Jul. 27, 2008, CAS Registry No. 1036533-91-1 (3 paqes).
Artavanis-Tsakonas et al., "Notch signalling: cell fate control and signal integration in development", Science 284(5415): 770-776.
Benzenamine, 4-[4-(I,I-dimethylethyl)phenoxy]-3-fluoro-, Sep. 12, 2007, CAS Registry No. 946785-77-9 (3 pages).
Benzenamine, 4-[4-(1,1-dimethylpropyl)phenoxy]-3-fluoro-, Sep. 12, 2007, CAS Registry No. 946742-50-3 (3 pages).
Bhatia, N. et al., Identification of novel small molecules that inhibit protein-protein interactions between MAGE and KAP-1:, Arch Biochem Biophys., 2011, vol. 508, No. 2, pp. 217-221.
Bray, S.J., "Notch siqnallinq: a simple becomes complex", Nature Rev Molec Cell Biol 7: 678-689, 2006.
De Houwer, J. et al. "Synthesis of Aryl(di)azinyl Ketones through Copper- and Iron-catalyzed Oxidation of the Methylene Group of Aryl(di)azinylmethanes." Angewandte Chemie International Edition, vol. 51, No. 11, Mar. 12, 2012, pp. 2745-2748.
Desbordes, S. G. et al., "High-Throughput Screening Assay for the Identification of Compounds Regulating Self-Renewal and Differentiation in Human Embryonic Stem Cells", Cell Stem Cell. Jun. 5, 2008; 2(6): 602-612.
Dittmer, D. P. et al. "Kaposi Sarcoma-Associated Herpesvirus: Immunobiology, Oncogenesis, and Therapy." The Journal of Clinical Investigation, vol. 126, No. 9, Sep. 1, 2016, pp. 3165-3175.
Emuss et al., "KSHV manipulates Notch sigrialing by DLL4 and JAGI to alter cell cycle genes in lymphatic endothelia", PLoS Pathog 5(10): el000616, 2009 (12 total pages).
European Extended Search Report, European Application No. 11010130.0, dated Jun. 6, 2012, 6 pages.
Friedman, H. L. et al. "Tuberculostatic Compounds. I. Ethers of 2-Hydroxy-5-Aminopyridine." J. Amer. Chem. Soc., vol. 69, 1947, pp. 1204-1206.
Harvard Medical School. "Comparison of Chemical Libraries." ICCB-Longwood Screening Facility, Aug. 2006, 1 page.
Hsiao, S-H. et al., "Electroactive aromatic polyamides and polyimides with adamantylphenoxy-substituted triphenylamine units", European Polymer Journal, vol. 45, Issue 8, 2009, pp. 2234-2248.
Huang, X. et al. "Late Stage Benzylic C—H Fluorination with [18F]fluoride for PET Imaging." Journal of the American Chemical Society, vol. 136, No. 19, May 14, 20174, pp. 6842-6845.
Ismail, H., et al., "Synthesis, Characterization, and Pharmacological Evaluation of Selected Aromatic Amines," Journal of Chemistry, Jan. 1, 2015, vol. 2015, pp. 1-9.
Jaleco et al., "Differential effects of Notch ligands Delta-1 and Jagged-1 in human lymphoid differentiation", J Exp Med 194(7): 991-1001, 2001.
Kavian, N. et al., "New insights into the mechanism of Notch signalling in fibrosis", Open Rheumatol J 6(Suppl 1: MS): 96-102, 2012.
Khim, S. K., et al., "Discovery of Novel and Potent Aryl Diamines as Leukotriene A4 Hydrolase Inhibitors," Bioorganic & Medicinal Chemistry Letters, Jul. 15, 2008, vol. 18, No. 14, pp. 3895-3898, Pergamon, Amsterdam, NL.
Laemmler, G., et al., "Chemotherapy of Fascioliases. IV. Action of Aromatic Amines Against Liver Flukes. 2," [Retrieved Online] Chemical Abstracts Service, Columbus, Ohio, US.
Langer, R. "New Methods of Drug Delivery." Science, vol. 249, No. 4976, Sep. 28, 1990, pp. 1527-1533.
Maybridge. "Browse HIT Finder." Plate 1 to 40, 1 page, [Online] [Retrieved Nov. 16, 2020], Retrieved from the internet <URL:http://www.chem.maybridge.com/hitfinder/>.
Maybridge. "Browse HIT Finder." Plate 121-160, 1 page, [Online] [Retrieved Nov. 16, 2020], Retrieved from the internet <URL:http://www.chem.maybridge.com/hitfinder/>.
Maybridge. "Browse HIT Finder." Plate 161-180, 1 page, [Online] [Retrieved Nov. 16, 2020], Retrieved from the internet <URL:http://www.chem.mavbridae.com/hitfinder/>.
Maybridge. "Browse HIT Finder." Plate 41-80, 1 page, [Online] [Retrieved Nov. 16, 2020], Retrieved from the internet <URL:http://www.chem.mavbridae.com/hitfinder/>.
Maybridge. "Browse HIT Finder." Plate 81-120, 1 page, [Online] [Retrieved Nov. 16, 2020], Retrieved from the internet <URL:http://www.chem.maybridge.com/hitfinder/>.
Maybridge. "Diversity Matters: Target Your Research with the HitFinger™ Collection of Screening Compounds." J. Chem. Inf. Comput. Sci., vol. 39, 1999, 1 page.
Mesri, E. A. et al. "Human Viral Oncogenesis: A Cancer Hallmark Analysis." Cell Host & Microbe, vol. 15, No. 3, Mar. 12, 2014, pp. 266-282.
Miele, L., "Transcription factor RBPJ/CSL: A genome-wide look at transcriptional regulation", Proc Natl Acad Sci USA 108(39): 14715-14716, 2011.
Oberbek et al., "Generation of stable, high-producing CHO cell lines by lentiviral vector-mediated gene transfer in serum-free suspension culture", Biotechnol Bioeng 108: 600-610, 2011.
PCT International Search Report and Written Opinion, PCT Application No. PCT/IB2012/057622, dated Apr. 26, 2013, 11 pages.
PCT International Search Report and Written Opinion, PCT Application No. PCT/EP2020/060153, dated May 29, 2020, 14 Pages.
PCT International Search Report and Written Opinion, PCT Application No. PCT/EP2020/060149, dated Jun. 19, 2020, 11 Pages.
Rosen, A. et al. "Lymphoblastoid Cell Line with B1 Cell Characteristics Established from a Chronic Lymphocytic Leukemia Clone by in Vitro EBV Infection." Oncolmmunology, vol. 1, No. 1, Jan. 1, 2012, pp. 18-27.
Sarmento, L. M. et al., "Therapeutic potential of Notch inhibition in T-cell acute lymphoblastic leukemia: rationale, caveats and promises", Expert Review of Anticancer Therapy, 2011, vol. 11, No. 9, pp. 1403-1415.
Schroeter et al., "Notch-1 signalling requires ligand-induced proteolytic release of intracelluar domain", Nature 3 93: 3 82-386, 1998.
Shih, I-M. et al. "Notch Signaling, γ-Secretase Inhibitors, and Cancer Therapy." Cancer Research, vol. 67, No. 5, Mar. 1, 2007, pp. 1879-1882.
Silverman, R. "The Organic Chemistry of Drug Design and Drug Action," 2004, Elsevier, excerpt, pp. 29-32.
Sun, M. et al., "Design, Synthesis, and In Vitro Antitumor Evaluation of Novel Diaryl Ureas Derivatives," European Journal of Medicinal Chemistry, Jun. 1, 2010, vol. 45, No. 6, Elsevier, Amsterdam, NL.
Taghavi, M., et al., "A Quick and Green Ionic Liquid-Mediated Approach for the Synthesis of High-Performance, Organosoluble and Thermally Stable Polyimides," Chinese Journal of Polymer Science, Mar. 9, 2013, vol. 31, No. 4, pp. 679-690.
Technology Networks. "Thermo Scientific Introduces Maybridge HitFinder-Plus Screening Compound Library." Technologynetworks.com, Dec. 16, 2011, 8 pages, [Online] [Retrieved Nov. 16, 2020], Retrieved from the internet <URL:https://www.technologynetworks.com/drug-discovery/product-news/thermo-scientific-introduces-mavbridae-hitfindernlus-screenina-comoound-librarv-224110>.
United States Office Action, U.S. Appl. No. 14/366,917, dated Mar. 3, 2015, seven pages.

(56) References Cited

OTHER PUBLICATIONS

United States Office Action, U.S. Appl. No. 15/017,986, dated Aug. 18, 2017, 16 pages.
United States Office Action, U.S. Appl. No. 15/017,986, dated Jun. 13, 2018, six pages.
United States Office Action, U.S. Appl. No. 16/363,336, dated Aug. 27, 2020, five pages.
United States Office Action, U.S. Appl. No. 16/363,336, dated Dec. 1, 2020, nine pages.
Written Opinion of International Search Authority dated Jun. 21, 2014, in International Application No. PCT/IB2012/057622.

* cited by examiner

PROCESS FOR MAKING AMINO DIARYL ETHERS AND AMINO DIARYL ETHERS HYDROCHLORIDE SALTS

FIELD OF THE INVENTION

The present invention relates to processes useful in the preparation of an amino diaryl ether of formula (I), in particular 6-(4-(tert-butyl)phenoxy)pyridin-3-amine (formula (Ia)).

The present invention further relates to a hydrochloride salt of the compound of formula (I) in particular a monohydrochloride salt of the compound of formula (I) and to processes useful in the preparation of said monohydrochloride salt of the compound of formula (I) in particular 6-(4-(tert-butyl)phenoxy)pyridin-3-amine (formula (Ia)).

BACKGROUND OF THE INVENTION

Compounds of Formula (I) are modulators of the Notch signalling pathway, useful in the treatment and/or prevention of cancer, in particular useful in the treatment and/or prevention of Notch-dependent cancer and may be prepared using the process disclosed in WO2013/093885. The process disclosed in WO2013/093885 suffers i.a. from the disadvantages that (i) the compounds of formula (I) obtained by said process are contaminated with the catalyst used and (ii) side reactions take place, leading to further contamination of the compounds of formula (I) with side products. These disadvantages affect e.g. physical appearance and solubility of the compounds of formula (I) and onward manufacturing steps like milling. In conclusion, the process described in WO2013/093885 is not suitable for large-scale production of pharmaceutical grade compounds of formula (I). It would thus be beneficial to develop alternative or improved processes for the production of compounds of Formula (I) that do not suffer from some or all of these disadvantages.

SUMMARY OF THE INVENTION

It has now surprisingly been found that contamination of compounds of formula (I) can be omitted by making them via the process comprising catalytic hydrogenation using a palladium catalyst in a solvent wherein the solvent is a polar, aprotic solvent or a C3-C10 alcohol. The inventive process has been found to be reliable and applicable on an industrial scale and the compounds of formula (I) achieved by the inventive process consistently have an unprecedented high level of purity (99.9% pure as determined by HPLC, Pd-content <1 ppm as determined by elemental analysis).

The inventors have surprisingly found that, when the compounds of formula (I) are transformed to their hydrochloride salts, stable salts were obtained whereas all attempts to form other acidic addition salts failed. The inventors have further surprisingly found that, when the compounds of formula (I) are transformed to their monohydrochloride salts, the level of purity is further increased in that said monohydrochloride salts are typically obtained as colourless, crystalline solids, whereas the colour of the respective free base varies from batch to batch (range from colourless to reddish), independent of the analytical level of purity.

Compounds disclosed in WO2013/093885, like 6-(4-(tert-butyl)phenoxy)pyridin-3-amine (formula (Ia)), have a quite low melting point of e.g. 92.0° C. (FIG. 2) which constitutes a certain risk regarding physical stability of the compound during manufacture, milling, storage and processing to pharmaceutical formulations. However, it has surprisingly been found that the monohydrochloride salts of the compounds of formula (I), e.g. 6-(4-(tert-butyl)phenoxy)pyridin-3-amine monohydrochloride (formula (Ia)), have a significantly higher melting point than the free base (e.g. 173° C., FIG. 1). Thus, monohydrochloride salts of the compounds of formula (I) surprisingly have improved properties with respect to the compounds of formula (I) in their free base form, such as higher melting points, improved solubilities in aqueous media and a discrete polymorph according to XRPD.

Taking these surprising findings into account, i.e. the high level of purity of the compounds of formula (I) achieved by the process of the invention and the favorable properties of the hydrochloride salts of the compound of formula (I), in particular of the monohydrochloride salts of the compounds of formula (I), the inventors herewith provide the present invention in its following aspects.

In a first aspect, the present invention provides a process for making a compound of formula (I)

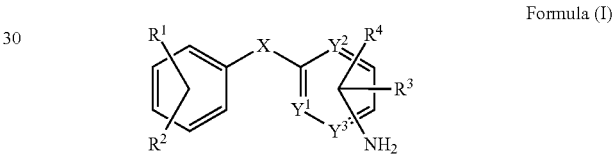

Formula (I)

wherein X is selected from O and NH; and wherein $Y^1$, $Y^2$ and $Y^3$ are each independently selected from N and CH; and wherein $R^1$ and $R^2$ are each independently selected from H, C1-C10 alkyl and C3-C12 cycloalkyl; and wherein $R^3$ and $R^4$ are each independently selected from H, halogen and C1-C10 alkyl comprising:

reducing a compound of formula (II) with hydrogen in the presence of a palladium catalyst and a solvent wherein the solvent is a polar, aprotic solvent or a C3-C10 alcohol

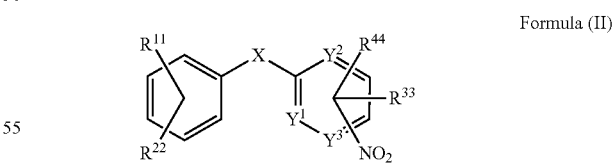

Formula (II)

wherein X is selected from O and NH; and wherein $Y^1$, $Y^2$ and $Y^3$ are each independently selected from N and CH; and wherein $R^{11}$ and $R^{22}$ are each independently selected from H, C1-C10 alkyl and C3-C12 cycloalkyl; and wherein $R^{33}$ and $R^{44}$ are each independently selected from H, halogen and C1-C10 alkyl;

to form said compound of formula (I).

In a second aspect, the present invention provides a process for making a hydrochloride salt of the compound of formula (I)

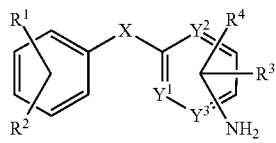

Formula (I)

wherein X is selected from O and NH; and
wherein Y¹, Y² and Y³ are each independently selected from N and CH; and
wherein R¹ and R² are each independently selected from H, C1-C10 alkyl and C3-C12 cycloalkyl; and
wherein R³ and R⁴ are each independently selected from H, halogen and C1-C10 alkyl comprising reacting said compound of formula (I) with hydrochloric acid.

In a third aspect, the present invention provides a process for making a monohydrochloride salt of the compound of formula (I)

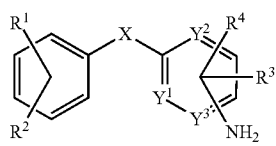

Formula (I)

wherein X is selected from O and NH; and
wherein Y¹, Y² and Y³ are each independently selected from N and CH; and
wherein R¹ and R² are each independently selected from H, C1-C10 alkyl and C3-C12 cycloalkyl; and
wherein R³ and R⁴ are each independently selected from H, halogen and C1-C10 alkyl comprising reacting said compound of formula (I) with less than 1.5 molar equivalents of hydrochloric acid.

In a fourth aspect, the present invention provides a hydrochloride salt of the compound of formula (I) as defined herein.

In a fifth aspect, the present invention provides a monohydrochloride salt of the compound of formula (I) as defined herein.

In a sixth aspect, the present invention provides a hydrochloride salt of the compound of formula (I) as defined herein for use as a medicament.

In a seventh aspect, the present invention provides a monohydrochloride salt of the compound of formula (I) as defined herein for use as a medicament.

In an eights aspect, the present invention provides a hydrochloride salt of the compound of formula (I) as defined herein for use in a method of treatment and/or prevention of cancer.

In a ninth aspect, the present invention provides a monohydrochloride salt of the compound of formula (I) as defined herein for use in a method of treatment and/or prevention of cancer.

BRIEF DESCRIPTION OF THE FIGURES

In the following the present invention is described in detail with reference to accompanying figures in which.

DETAILED DESCRIPTION OF THE INVENTION

Figure 1:
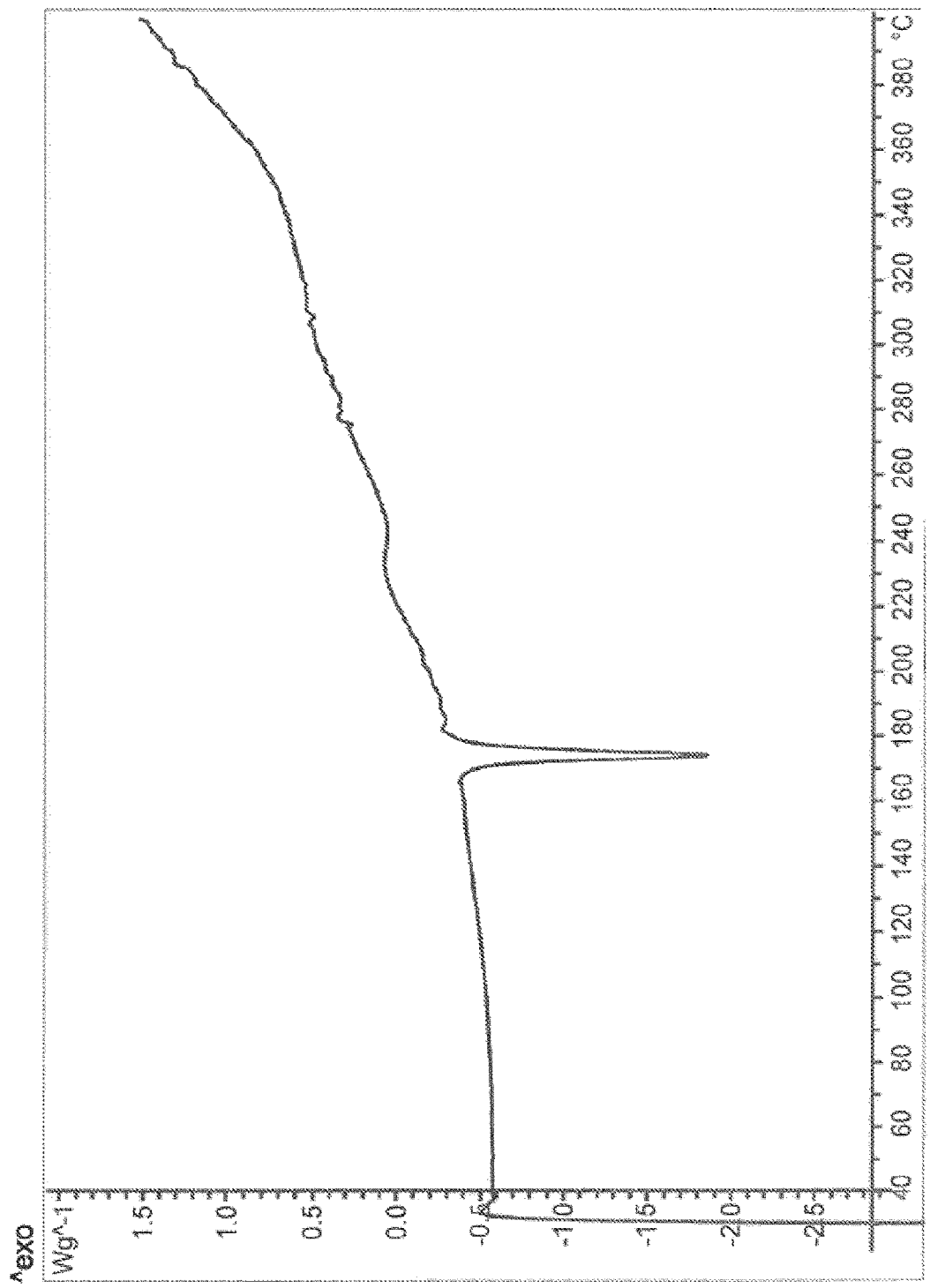
FIG. 1 shows a differential scanning calorimetry thermogram (DSC) of the monohydrochloride salt of the compound of formula (Ia), i.e. 6-(4-(tert-butyl)phenoxy)pyridin-3-amine monohydrochloride. The DSC thermogram indicates that 6-(4-(tert-butyl)phenoxy)pyridin-3-amine monohydrochloride has a melting point with an onset of 170.9° C. and peaking at 173.4° C.

Hereinafter, the present invention is described in further detail and is exemplified.

Definitions

The term "about" refers to +/−10% of a given measurement.

The term "polar, aprotic solvent" refers to solvents which do not contain acidic hydrogen (Morrison and Boyd, Organic Chemistry 3rd. Edition, 31 (1974)) and which have a polarity according to the $E_T(30)$-Scale of between about 36 kcal/mol and about 49 kcal/mol (C. Reichardt, Chem. Rev. 1994, 94, 2319-2358; C. Reichardt, G. Schafer, Liebigs Ann. 1995, 1579-1582; R. Eberhardt, S. Löbbecke, B. Neidhart, C. Reichardt, Liebigs Ann./Recueil 1997, 1195-1199; C. Reichardt, Green Chem. 2005, 7, 339-351; V. G. Machado, R. I. Stock, C. Reichardt, Chem. Rev. 2014, 114, 10429-10475.). The proton donating or proton accepting interaction is usually greatest when the atom attached to the proton is nitrogen or oxygen. This behavior has been attributed to hydrogen bonding. In general, the hydrogen bond strength increases with increasing acidity of the proton-donating group, and increasing basicity of the proton-accepting group. Polar, aprotic solvents suitable for use in this invention will be those solvents that do not contain acidic or basic functional groups and do not degrade into acids or bases, including, but not limited to, ketones, nitriles, substituted aromatics such as halogenated aromatics, amides, sulfoxides, alkyl carbonates, chlorinated aliphatics, aromatic aldehydes, sulfones, esters, and the like, or mixtures thereof. The preferred polar, aprotic solvents for use in this invention include, but are not limited to, acetone, 2-butanone, 3-methyl-2-butanone, cyclohexanone, acetonitrile, chlorobenzene, methylene chloride, chloroform, trichloroethane, ethylene chloride, benzaldehyde, sulfolane, ethyl acetate, propyl acetate, amyl acetate, dimethyl sulfoxide (DMSO), dimethylformamide (DMF), dimethylacetamide, diethylcarbonate, propylene carbonate, ethylene carbonate, methyl ethyl ketone, methyl isopropyl ketone, methyl isobutyl ketone, and mixtures thereof. Various other solvents having the above polar and aprotic characteristics are known to those skilled in the art.

The term "C3-C10 alcohol" refers to a unsubstituted linear or branched alkanol group comprising 3-10 carbon atoms, preferably a unsubstituted linear or branched alkanol group comprising 3-5 carbon atoms e.g. 1-propanol, 2-propanol, 2-butanol, 2-Methyl-1-propanol, or 2-Methylpropan-2-ol, more preferably 2-butanol or 2-propanol, most preferably 2-propanol.

The term "non-polar solvent" refers to a solvent having a polarity according to the $E_T(30)$-Scale of less than about 35 kcal/mol. The preferred non-polar solvents for use in this invention include, but are not limited to, pentane, hexane, heptane, cyclohexane and toluene, in particular heptane. When the non-polar solvent is e.g. a C5-C8-alkane, such as pentane, hexane or heptane, said C5-C8-alkane may be isomerically pure (e.g. n-pentane, n-hexane or n-heptane) or a random mixture of constitutional isomers.

The term "protic solvent" refers to a solvent comprising a proton-donating group. Non-limiting examples of protic solvents are e.g. water.

The expression "Tout" refers to the outer temperature measured outside a reactor and the expression "Ti" refers to the internal temperature measured inside a reactor. When a reaction temperature is indicated without specifying "Tout" or "Ti", it is understood that the temperature is measured outside the reactor.

The term "alkyl" refers to an unsubstituted linear or branched alkyl group, preferably an unsubstituted linear or branched alkyl group comprising 1-10 carbon atoms ("C1-C10 alkyl"), more preferably an unsubstituted linear or branched alkyl group comprising 3-8 carbon atoms ("C3-C8 alkyl"). Non-limiting examples of alkyl groups are methyl, ethyl, n-propyl, iso-propyl, n-butyl, sec-butyl, tert-butyl, 1,1-dimethylpropyl, 1,1-dimethyl-3,3-dimethylbutyl and 1,1-dimethylbutyl. A particularly preferred alkyl group is tert-butyl.

The term "halogen" refers to fluorine, chlorine, bromine or iodine.

The term "cycloalkyl" refers to unsubstituted monocyclic, bicyclic, tricyclic or tetracyclic hydrocarbon groups of 3 to 12 carbon atoms ("C3-C12 cycloalkyl"), preferably of 5 to 10 carbon atoms ("C5-C10 cycloalkyl"). Non-limiting examples of cycloalkyl groups are cyclopropyl, cyclobutyl, cyclopentyl, cyclohexyl and adamantyl. Particularly preferred cycloalkyl groups are cyclohexyl and adamantyl.

The term "activated charcoal" refers to a form of carbon processed to have small, low-volume pores that increase the surface area available for adsorption or chemical reactions. Activated charcoal has a surface area in excess of 500 m$^2$/g. Typically, the surface area of activated charcoal is about 1000 m$^2$/g, but it may be up to 3000 m$^2$/g. A non-limiting example of activated charcoal is activated charcoal having an iodine absorption (0.05 mol $I_2$/l) of >70 mL/g and/or a methylene blue-absorption (0.15% sol.) of >12 mL/0.1 g or having an iodine absorption of 1200 mg/g and/or a methylene blue-absorption of 255 mg/g.

The term "base" refers to a chemical compound that deprotonates another compound when reacted with it. Suitable bases for use in accordance with this disclosure include but are not limited to, e.g., tertiary amines, organolithium compounds and basic alkaline metal salts and hydrides. Examples of tertiary amines include triethylamine, N-methylmorpholine and diisopropylethylamine. Examples of organolithium compounds include methyllithium (CH$_3$Li, MeLi), n-butyllithium (n-BuLi), sec-butyllithium (sec-BuLi) and tert-butyllithium (tert-BuLi). Examples of basic alkaline metal hydrides and salts include, e.g., sodium hydride (NaH), potassium hydride (KH), sodium carbonate (Na$_2$CO$_3$), potassium carbonate (K$_2$CO$_3$), sodium bicarbonate (NaHCO$_3$), sodium and potassium alkoxides including, but not limited to, sodium and potassium t-butoxide, propoxide, i-propoxide, ethoxide, methoxide, and the like, sodium amide (NaNH$_2$), potassium amide (KNH$_2$), and the like. Preferred bases are MeLi, K$_2$CO$_3$ and Na$_2$CO$_3$.

The term "hydrochloride salt" refers to the compound of formula (I) or (Ia), respectively, wherein said compound of formula (I) or (Ia) is protonated and the counterion is chloride (Cr) and comprises mono- and/or dichloride salts, in particular a mixture of mono- and dichloride salts.

The term "monohydrochloride salt" refers to the compound of formula (I) or (Ia), respectively, wherein said compound of formula (I) or (Ia) is protonated once and the counterion is chloride (Cl$^-$). Thus, the stoichiometry of mono-protonated compound of formula (I) or (Ia) to chloride is 1:1.

The term "purity" is expressed in percent (%) and is calculated from an HPLC chromatogram recorded at 220 nm according to the following formula:

purity of compound of formula$(I)=(A_I/A_x)\times 100$, wherein $A_I$ is the area of the peak corresponding to the compound of formula (I), e.g. the compound of formula (Ia) and $A_x$ is the sum of the areas of all other peaks observed in the HPLC chromatogram.

Process for Making Compounds of Formula (I)

In a first aspect, the present invention provides a process for making a compound of formula (I)

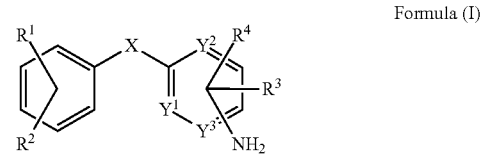

Formula (I)

wherein X is selected from 0 and NH; and
wherein Y$^1$, Y$^2$ and Y$^3$ are each independently selected from N and CH; and
wherein R$^1$ and R$^2$ are each independently selected from H, C1-C10 alkyl and C3-C12 cycloalkyl; and
wherein R$^3$ and R$^4$ are each independently selected from H, halogen and C1-C10 alkyl, comprising:
reducing a compound of formula (II) with hydrogen in the presence of a palladium catalyst and a solvent wherein the solvent is a polar, aprotic solvent or a C3-010 alcohol

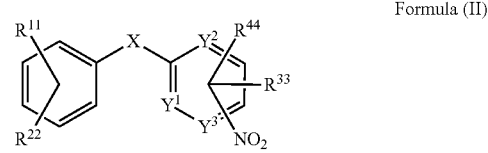

Formula (II)

wherein X is selected from O and NH; and wherein $Y^1$, $Y^2$ and $Y^3$ are each independently selected from N and CH; and wherein $R^{11}$ and $R^{22}$ are each independently selected from H, C1-C10 alkyl and C3-C12 cycloalkyl; and wherein $R^{33}$ and $R^{44}$ are each independently selected from H, halogen and C1-C10 alkyl;

to form said compound of formula (I).

In one embodiment, there is provided a process according to the first aspect of the invention wherein the palladium catalyst is palladium on activated charcoal.

In a preferred embodiment, there is provided a process according to the first aspect of the invention wherein said palladium catalyst is palladium on activated charcoal selected from palladium on activated charcoal comprising about 10% wt/wt palladium and palladium on activated charcoal comprising about 5% wt/wt palladium, in particular palladium on activated charcoal comprising about 5% wt/wt palladium.

In one embodiment, there is provided a process according to the first aspect of the invention wherein said reduction of the compound of formula (II) to afford the compound of formula (I) comprises:
(a) providing a solution of the compound of formula (II) in a solvent wherein the solvent is a polar, aprotic solvent or a C3-C10 alcohol; followed by
(b) adding the palladium catalyst to the solution of step (a); and
(c) contacting the mixture obtained in step (b) with hydrogen;
wherein said palladium catalyst added in step (b) is added as a dry powder or as a suspension in the solvent used in step (a), preferably as a suspension in the solvent used in step (a).

In a further embodiment, there is provided a process according to the first aspect of the invention wherein the amount of palladium relative to the compound of formula (II) is less than 7 mol %, preferably less than about 6 mol %, more preferably less than about 5 mol %, more preferably less than about 4 mol %, more preferably less than about 3 mol %, more preferably less than about 2 mol %, in particular about 1.25 mol %.

In a further embodiment, there is provided a process according to the first aspect of the invention wherein the amount of palladium relative to the compound of formula (II) is less than 7 mol % and equal or higher than 1 mol %, preferably less than about 6 mol % and equal or higher than 1 mol %, more preferably less than about 5 mol % and equal or higher than 1 mol %, more preferably less than about 4 mol % and equal or higher than 1 mol %, more preferably less than about 3 mol % and equal or higher than 1 mol %, more preferably less than about 2 mol % and equal or higher than 1 mol %, in particular about 1.25 mol %.

In a preferred embodiment, there is provided a process according to the first aspect of the invention wherein the solvent is selected from 2-propanol, acetone, 2-butanone, 3-methyl-2-butanone, cyclohexanone, acetonitrile, chlorobenzene, methylene chloride, chloroform, trichloroethane, ethylene chloride, benzaldehyde, sulfolane, ethyl acetate, propyl acetate, amyl acetate, dimethylsulfoxide (DMSO), dimethylformamide (DMF), dimethylacetamide, diethylcarbonate, propylene carbonate, ethylene carbonate, methyl ethyl ketone, methyl isopropyl ketone, methyl isobutyl ketone and mixtures thereof.

In a further preferred embodiment, there is provided a process according to the first aspect of the invention wherein the solvent is selected from 2-propanol, acetone, 2-butanone, 3-methyl-2-butanone, cyclohexanone, acetonitrile, chlorobenzene, methylene chloride, chloroform, trichloroethane, ethylene chloride, benzaldehyde, sulfolane, ethyl acetate, propyl acetate, amyl acetate, dimethylsulfoxide (DMSO), dimethylformamide (DMF), dimethylacetamide, diethylcarbonate, propylene carbonate, ethylene carbonate and mixtures thereof.

In a more preferred embodiment, there is provided a process according to the first aspect of the invention wherein the solvent is a polar, aprotic solvent.

In an even more preferred embodiment, there is provided a process according to the first aspect of the invention wherein the solvent is selected from acetone, 2-butanone, 3-methyl-2-butanone, cyclohexanone, acetonitrile, chlorobenzene, methylene chloride, chloroform, trichloroethane, ethylene chloride, benzaldehyde, sulfolane, ethyl acetate, propyl acetate, amyl acetate, dimethylsulfoxide (DMSO), dimethylformamide (DMF), dimethylacetamide, diethylcarbonate, propylene carbonate, ethylene carbonate, methyl ethyl ketone, methyl isopropyl ketone, methyl isobutyl ketone and mixtures thereof.

In a further even more preferred embodiment, there is provided a process according to the first aspect of the invention wherein the solvent is selected from acetone, 2-butanone, 3-methyl-2-butanone, cyclohexanone, acetonitrile, chlorobenzene, methylene chloride, chloroform, trichloroethane, ethylene chloride, benzaldehyde, sulfolane, ethyl acetate, propyl acetate, amyl acetate, dimethylsulfoxide (DMSO), dimethylformamide (DMF), dimethylacetamide, diethylcarbonate, propylene carbonate, ethylene carbonate and mixtures thereof.

In a particular preferred embodiment, there is provided a process according to the first aspect of the invention wherein the solvent is ethyl acetate or 2-propanol.

In a more particular preferred embodiment, there is provided a process according to the first aspect of the invention wherein the solvent is ethyl acetate.

The inventors have surprisingly found that the process according to the invention allows for a shorter reaction time than the prior art process described in WO2013/093885. Accordingly, in one embodiment, there is provided a process according to the first aspect of the invention, wherein the reduction of said compound of formula (II) to said compound of formula (I) is complete after 1-3 h, preferably after 1.5-3 h, more preferably after 2-3 h, e.g. after 2.5 h, preferably when performed using 1.2 kg of the compound of formula (II). In a further embodiment, there is provided a process according to the first aspect of the invention, wherein the reduction of said compound of formula (II) to said compound of formula (I) is complete after 0.5-1.5 h, preferably after 40 min, preferably when performed using 300 g of the compound of formula (II).

In a further embodiment, there is provided a process according to the first aspect of the invention, further comprising contacting the compound of formula (I) with activated charcoal.

In a further embodiment, there is provided a process according to the first aspect of the invention, further comprising crystallizing the compound of formula (I).

In a preferred embodiment, there is provided a process according to the first aspect of the invention, further comprising contacting the compound of formula (I) with activated charcoal; and crystallizing the compound of formula (I).

In a further embodiment, there is provided a process according to the first aspect of the invention, further comprising crystallizing the compound of formula (I), wherein said crystallizing comprises precipitating the compound of formula (I) in crystalline form from a solvent mixture comprising a solvent as described herein, preferably a polar, aprotic solvent used in the reduction of the compound of formula (II), and a non-polar solvent.

In a preferred embodiment, there is provided a process according to the first aspect of the invention, further comprising crystallizing the compound of formula (I), wherein said crystallizing comprises precipitating the compound of formula (I) in crystalline form from a solvent mixture comprising ethyl acetate and heptane.

In a further embodiment, there is provided a process according to the first aspect of the invention, wherein the starting material of formula (II) is obtained by a process comprising reacting a compound of formula (III)

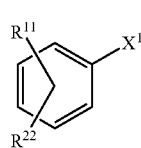

Formula (III)

wherein $X^1$ is selected from OH and $NH_2$; and
wherein $R^{11}$ and $R^{22}$ are each independently selected from H, C1-C10 alkyl and C3-C12 cycloalkyl
with a compound of formula (IV)

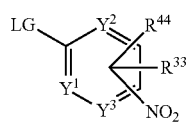

Formula (IV)

wherein LG is a leaving group; and
wherein $Y^1$, $Y^2$ and $Y^3$ are each independently selected from N and CH; and
wherein $R^{33}$ and $R^{44}$ are each independently selected from H, halogen and C1-C10 alkyl;
in the presence of a base to form said starting material of formula (II) wherein X is O or NH, wherein $R^{11}$ and $R^{22}$ are as defined for the compound of formula (III); and wherein $R^{33}$, $R^{44}$, $Y^1$, $Y^2$ and $Y^3$ are as defined for the compound of formula (IV); and optionally further comprising crystallizing said starting material of formula (II).

In one embodiment the leaving group LG is selected from the group consisting of F, Cl, Br, mesylate, tosylate and triflate. Preferably, the leaving group LG is selected from the group consisting of F, Cl, and Br.

In a preferred embodiment, there is provided a process according to the first aspect of the invention, wherein the starting material of formula (II) is obtained by a process comprising reacting a compound of formula (III) as defined above, with a compound of formula (IV) as defined above in the presence of a base in a polar, aprotic solvent, preferably in a polar, aprotic solvent selected from dimethyl sulfoxide (DMSO), dimethyl formamide (DMF) or a mixture thereof, most preferably in DMSO, to form said starting material of formula (II).

In a preferred embodiment, there is provided a process according to the first aspect of the invention, wherein the starting material of formula (II) is obtained by a process comprising reacting a compound of formula (III) as defined above, with a compound of formula (IV) as defined above in the presence of a base to form said starting material of formula (II), and optionally further comprising crystallizing said starting material of formula (II), wherein said base is selected from the group consisting of potassium carbonate ($K_2CO_3$), sodium carbonate ($Na_2CO_3$), cäsium carbonate ($Cs_2CO_3$) $NEt_3$, Hünigs base and 1,8-Diazabicyclo[5.4.0]undec-7-en (DBU), preferably selected from the group consisting of potassium carbonate ($K_2CO_3$), sodium carbonate ($Na_2CO_3$) and cäsium carbonate ($Cs_2CO_3$). More preferably said base is potassium carbonate ($K_2CO_3$).

In a further preferred embodiment, there is provided a process according to the first aspect of the invention, wherein the starting material of formula (II) is obtained by a process comprising reacting a compound of formula (III) as defined above, with a compound of formula (IV) as defined above in the presence of a base in a polar, aprotic solvent, preferably in a polar, aprotic solvent selected from dimethyl sulfoxide (DMSO), dimethyl formamide (DMF) or a mixture thereof, most preferably in DMSO, to form said starting material of formula (II); and optionally further comprising crystallizing said starting material of formula (II), wherein said crystallizing comprises precipitating the starting material of formula (II) in crystalline form from a solvent mixture comprising a polar, aprotic solvent and a non-polar solvent, preferably from a solvent mixture comprising ethyl acetate and heptane.

In a particularly preferred embodiment, there is provided a process according to the first aspect of the invention, wherein said compound of formula (I) is 6-(4-(tert-butyl)phenoxy)pyridin-3-amine (formula (Ia));

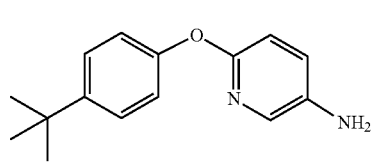

Formula (Ia)

and wherein said compound of formula (II) is 2-(4-(tert-butyl)phenoxy)-5-nitropyridine (Formula (IIa));

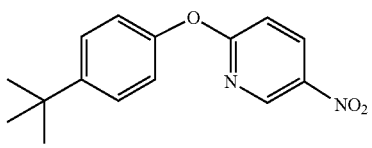

Formula (IIa)

and optionally wherein the starting material of formula (IIa) is obtained by a process comprising reacting 4-(tert-butyl)-phenol (formula (IIIa))

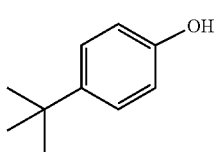

Formula (IIIa)

with 2-chloro-5-nitro-pyridine (formula (IVa))

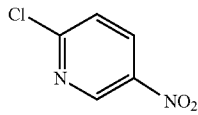

Formula (IVa)

in the presence of a base to form 2-(4-(tert-butyl)phenoxy)-5-nitropyridine (Formula (IIa)), and optionally further comprising crystallizing said 2-(4-(tert-butyl)phenoxy)-5-nitropyridine (Formula (IIa)).

Thus the present invention provides a process for making a compound of formula (Ia)

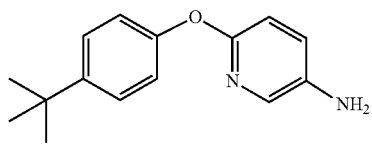

Formula (Ia)

comprising:
reducing a compound of formula (IIa) with hydrogen in the presence of a palladium catalyst and a solvent wherein the solvent is a polar, aprotic solvent or a C3-C10 alcohol

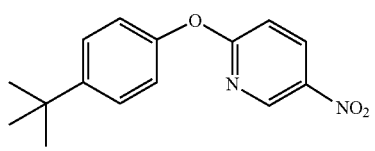

Formula (IIa)

to form said compound of formula (Ia).

In a further particularly preferred embodiment, there is provided a process according to the first aspect of the invention,
wherein said compound of formula (I) is 6-(4-(tert-butyl)phenoxy)pyridin-3-amine (formula (Ia)); and
wherein the starting material of formula (II) is 2-(4-(tert-butyl)phenoxy)-5-nitropyridine (Formula (IIa)); and
wherein the starting material of formula (IIa) is obtained by a process comprising reacting 4-(tert-butyl)-phenol (formula (IIIa)) with 2-chloro-5-nitro-pyridine (formula (IVa)) in the presence of a base to form 2-(4-(tert-butyl)phenoxy)-5-nitropyridine (Formula (IIa)); and
further comprising crystallizing said 2-(4-(tert-butyl)phenoxy)-5-nitropyridine (formula (IIa), wherein 2-(4-(tert-butyl)phenoxy)-5-nitropyridine (Formula (IIa)) is precipitated in crystalline form from a solvent mixture comprising ethyl acetate and heptane.

In a further particularly preferred embodiment of the first aspect of the invention, the present invention provides a process for making 6-(4-(tert-butyl)phenoxy)pyridin-3-amine (formula (Ia)), comprising reducing 2-(4-(tert-butyl)phenoxy)-5-nitropyridine (Formula (IIa)) with hydrogen in the presence of palladium on activated charcoal and ethyl acetate to form 6-(4-(tert-butyl)phenoxy)pyridin-3-amine (formula (Ia)).

In a further particularly preferred embodiment of the first aspect of the invention, the present invention provides a process for making 6-(4-(tert-butyl)phenoxy)pyridin-3-amine (formula (Ia)) comprising reducing 2-(4-(tert-butyl)phenoxy)-5-nitropyridine (Formula (IIa)) with hydrogen in the presence of palladium on activated charcoal and ethyl acetate to form 6-(4-(tert-butyl)phenoxy)pyridin-3-amine (formula (Ia)); wherein the amount of palladium relative to the compound of formula (IIa) is less than 7 mol %, preferably less than about 6 mol %, more preferably less than about 5 mol %, more preferably less than about 4 mol %, more preferably less than about 3 mol %, more preferably less than about 2 mol %, in particular about 1.25 mol %.

In a further particularly preferred embodiment of the first aspect of the invention, the present invention provides a process for making 6-(4-(tert-butyl)phenoxy)pyridin-3-amine (formula (Ia)) comprising reducing 2-(4-(tert-butyl)phenoxy)-5-nitropyridine (Formula (IIa)) with hydrogen in the presence of palladium on activated charcoal and ethyl acetate to form 6-(4-(tert-butyl)phenoxy)pyridin-3-amine (formula (Ia)); wherein the amount of palladium relative to the compound of formula (IIa) is less than 7 mol % and equal or higher than 1 mol %, preferably less than about 6 mol % and equal or higher than 1 mol %, more preferably less than about 5 mol % and equal or higher than 1 mol %, more preferably less than about 4 mol % and equal or higher than 1 mol %, more preferably less than about 3 mol % and equal or higher than 1 mol %, more preferably less than about 2 mol % and equal or higher than 1 mol %, in particular about 1.25 mol %.

In a further particularly preferred embodiment of the first aspect of the invention, the present invention provides a process for making 6-(4-(tert-butyl)phenoxy)pyridin-3-amine (formula (Ia)) comprising reducing 2-(4-(tert-butyl)phenoxy)-5-nitropyridine (Formula (IIa)) with hydrogen in the presence of palladium on activated charcoal and ethyl acetate to form 6-(4-(tert-butyl)phenoxy)pyridin-3-amine (formula (Ia));
wherein said reduction of 2-(4-(tert-butyl)phenoxy)-5-nitropyridine (Formula (IIa)) with hydrogen comprises:
(a) providing a solution of 2-(4-(tert-butyl)phenoxy)-5-nitropyridine (Formula (IIa)) in ethyl acetate; followed by
(b) adding palladium on charcoal to the solution of step (a); and
(c) contacting the suspension obtained in step (b) with hydrogen;
wherein the palladium on activated charcoal added in step (b) is added as a dry powder or as a suspension in ethyl acetate, preferably as a suspension in ethyl acetate.

Compounds of Formula (I)

Preferably the group $NH_2$ is in position 4 (para) with respect to group X of the ring having groups $Y^1$, $Y^2$ and $Y^3$. Preferably the groups $R^1$ or $R^2$ are in position 3 (meta) or 4 (para) with respect to group X of the ring without groups $Y^1$, $Y^2$ and $Y^3$, more preferably $R^1$ is in position 4 (para) with respect to group X of the ring without groups $Y^1$, $Y^2$ and $Y^3$, whereas $R^2$ is H, even more preferably $R^1$ is H, whereas $R^2$ is in position 4 (para) with respect to group X of the ring without groups $Y^1$, $Y^2$ and $Y^3$. Preferably the group $R^3$ or $R^4$ are in position 2 (ortho) (provided $Y^2$ and/or $Y^1$ is C) with respect to group X of the ring having groups $Y^1$, $Y^2$ and $Y^3$. More preferably $R^3$ is in position 2 (ortho) (provided $Y^2$ and/or $Y^1$ is C) with respect to group X of the ring having groups $Y^1$, $Y^2$ and $Y^3$, whereas $R^4$ is H, even more preferably $R^3$ is H, whereas $R^4$ is in position 2 (ortho) (provided $Y^2$ and/or $Y^1$ is C) with respect to group X of the ring having groups $Y^1$, $Y^2$ and $Y^3$. Preferably the groups $R^{11}$ or $R^{22}$ are in position 3 (meta) or 4 (para) with respect to group X of the ring without groups $Y^1$, $Y^2$ and $Y^3$, more preferably $R^{11}$ is in position 4 (para) with respect to group X of the ring without groups $Y^1$, $Y^2$ and $Y^3$, whereas $R^{22}$ is H, even more preferably $R^{11}$ is H, whereas $R^{22}$ is in position 4 (para) with respect to group X of the ring without groups $Y^1$, $Y^2$ and $Y^3$. Preferably the group $R^{33}$ or $R^{43}$ are in position 2 (ortho) (provided $Y^2$ and/or $Y^1$ is C) with respect to group X of the ring having groups $Y^1$, $Y^2$ and $Y^3$, more preferably $R^{33}$ is in position 2 (ortho) (provided $Y^2$ and/or $Y^1$ is C) with respect to group X of the ring having groups $Y^1$, $Y^2$ and $Y^3$, whereas $R^{44}$ is H, even more preferably $R^{33}$ is H, whereas $R^{43}$ is in position 2 (ortho) (provided $Y^2$ and/or $Y^1$ is C) with respect to group X of the ring having groups $Y^1$, $Y^2$ and $Y^3$.

In a preferred embodiment, there is provided a process according to the first aspect of the invention, wherein for said compound of formula (I) X is O; and wherein for said compound of formula (II) X is O.

In a further embodiment, there is provided a process according to the first aspect of the invention, wherein for said compound of formula (I)
  $Y^1$, $Y^2$ and $Y^3$ are each selected from N and CH, wherein at least one of $Y^1$, $Y^2$ and $Y^3$ is CH; and
  wherein for said compound of formula (II) $Y^1$, $Y^2$ and $Y^3$ are each selected from N and CH, wherein at least one of $Y^1$, $Y^2$ and $Y^3$ is CH.

In a further embodiment, there is provided a process according to the first aspect of the invention, wherein for said compound of formula (I)
  $Y^1$, $Y^2$ and $Y^3$ are each selected from N and CH, wherein at least one of $Y^1$ and $Y^3$ is CH; and
  wherein for said compound of formula (II) $Y^1$, $Y^2$ and $Y^3$ are each selected from N and CH,
  wherein at least one of $Y^1$ and $Y^3$ is CH.

In a preferred embodiment, there is provided a process according to the first aspect of the invention, wherein for said compound of formula (I)
  $Y^1$ is selected from N and CH; and
  $Y^2$ and $Y^3$ are each CH; and
  wherein for said compound of formula (II)
  $Y^1$ is selected from N and CH; and $Y^2$ and $Y^3$ are each CH.

In a more preferred embodiment, there is provided a process according to the first aspect of the invention, wherein for said compound of formula (I)
  $Y^1$ is N; and
  $Y^2$ and $Y^3$ are each CH; and
  wherein for said compound of formula (II)
  $Y^1$ is N; and $Y^2$ and $Y^3$ are each CH.

In one embodiment, there is provided a process according to the first aspect of the invention, wherein for said compound of formula (I) $R^1$ and $R^2$ are each independently selected from H and C1-C10 alkyl; and wherein for said compound of formula (II) $R^{11}$ and $R^{22}$ are each independently selected from H and C1-C10 alkyl.

In a further embodiment, there is provided a process according to the first aspect of the invention, wherein for said compound of formula (I) $R^1$ and $R^2$ are each independently selected from H and C3-C12 cycloalkyl; and wherein for said compound of formula (II) $R^{11}$ and $R^{22}$ are each independently selected from H and C3-C12 cycloalkyl.

In a preferred embodiment, there is provided a process according to the first aspect of the invention, wherein for said compound of formula (I) $R^1$ is H and $R^2$ is selected from H, C1-C10 alkyl and C3-C12 cycloalkyl; and wherein for said compound of formula (II) $R^{11}$ is H and $R^{22}$ is selected from H, C1-C10 alkyl and C3-C12 cycloalkyl.

In a further preferred embodiment, there is provided a process according to the first aspect of the invention, wherein for said compound of formula (I) $R^1$ is H and $R^2$ is selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and wherein for said compound of formula (II) $R^{11}$ is H and $R^{22}$ is selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl.

In a particularly preferred embodiment, there is provided a process according to the first aspect of the invention, wherein for said compound of formula (I) $R^1$ is H and $R^2$ is tert-butyl; and wherein for said compound of formula (II) $R^{11}$ is H and $R^{22}$ is tert-butyl.

In one embodiment, there is provided a process according to the first aspect of the invention, wherein for said compound of formula (I) $R^3$ and $R^4$ are each independently selected from H, and halogen; and wherein for said compound of formula (II) $R^{33}$ and $R^{44}$ are each independently selected from H, and halogen.

In one embodiment, there is provided a process according to the first aspect of the invention, wherein for said compound of formula (I) $R^3$ and $R^4$ are both halogen, preferably fluorine; and wherein for said compound of formula (II) $R^{33}$ and $R^{44}$ are both halogen, preferably fluorine.

In a preferred embodiment, there is provided a process according to the first aspect of the invention, wherein for said compound of formula (I) $R^3$ is H and $R^4$ is selected from H and halogen, preferably from H and fluorine; and wherein for said compound of formula (II) $R^{33}$ is H and $R^{44}$ is selected from H, and halogen, preferably from H and fluorine.

In a particularly preferred embodiment, there is provided a process according to the first aspect of the invention, wherein for said compound of formula (I) $R^3$ and $R^4$ are both H; and wherein for said compound of formula (II) $R^{33}$ and $R^{44}$ are both H.

In one embodiment, there is provided a process according to the first aspect of the invention, wherein for said compound of formula (I)
  X is selected from O and NH; and
  $Y^1$, $Y^2$ and $Y^3$ are each selected from N and CH, wherein at least one of $Y^1$, $Y^2$ and $Y^3$ is CH; and
  $R^1$ and $R^2$ are each independently selected from H, C1-C10 alkyl and C3-C12 cycloalkyl; and
  $R^3$ and $R^4$ are each independently selected from H and halogen; and wherein for said compound of formula (II)
  X, $Y^1$, $Y^2$ and $Y^3$ are as defined for the compound of formula (I); and $R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)
  X is selected from O and NH; and
  $Y^1$, $Y^2$ and $Y^3$ are each selected from N and CH, wherein at least one of $Y^1$ and $Y^3$ is CH; and
  $R^1$ and $R^2$ are each independently selected from H, C1-C10 alkyl and C3-C12 cycloalkyl; and
  $R^3$ and $R^4$ are each independently selected from H and halogen; and wherein for said compound of formula (II)
  X, $Y^1$, $Y^2$ and $Y^3$ are as defined for the compound of formula (I); and
  $R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)
- X is selected from O and NH; and
- $Y^1$ is selected from N and CH; and
- $Y^2$ and $Y^3$ are each CH; and
- $R^1$ and $R^2$ are each independently selected from H, C1-C10 alkyl and C3-C12 cycloalkyl; and
- $R^3$ and $R^4$ are each independently selected from H and halogen; and wherein for said compound of formula (II)
- X, $Y^1$, $Y^2$ and $Y^3$ are as defined for the compound of formula (I); and
- $R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)
- X is selected from O and NH; and
- $Y^1$ is selected from N and CH; and
- $Y^2$ and $Y^3$ are each CH; and
- $R^1$ is H and $R^2$ is selected from H, C1-C10 alkyl and C3-C12 cycloalkyl; and
- $R^3$ and $R^4$ are each independently selected from H and halogen; and
- wherein for said compound of formula (II)
- X, $Y^1$, $Y^2$ and $Y^3$ are as defined for the compound of formula (I); and
- $R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)
- X is selected from O and NH; and
- $Y^1$ is selected from N and CH; and
- $Y^2$ and $Y^3$ are each CH; and
- $R^1$ is H and $R^2$ is selected from H, C1-C10 alkyl and C3-C12 cycloalkyl; and
- $R^3$ is H and $R^4$ is selected from H and halogen; and
- wherein for said compound of formula (II)
- X, $Y^1$, $Y^2$ and $Y^3$ are as defined for the compound of formula (I); and
- $R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)
- X is selected from O and NH; and
- $Y^1$ is selected from N and CH; and
- $Y^2$ and $Y^3$ are each CH; and
- $R^1$ is H and $R^2$ is selected from H, C3-C8 alkyl and C5-C10 cycloalkyl; and
- $R^3$ is H and $R^4$ is selected from H and halogen; and
- wherein for said compound of formula (II)
- X, $Y^1$, $Y^2$ and $Y^3$ are as defined for the compound of formula (I); and
- $R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)
- X is selected from O and NH; and
- $Y^1$ is selected from N and CH; and
- $Y^2$ and $Y^3$ are each CH; and
- $R^1$ is H and $R^2$ is selected from H and C3-C8 alkyl; and
- $R^3$ is H and $R^4$ is selected from H and halogen; and
- wherein for said compound of formula (II)
- X, $Y^1$, $Y^2$ and $Y^3$ are as defined for the compound of formula (I); and
- $R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)
- X is selected from O and NH; and
- $Y^1$ is selected from N and CH; and
- $Y^2$ and $Y^3$ are each CH; and
- $R^1$ is H and $R^2$ is selected from H and C5-C10 cycloalkyl; and
- $R^3$ is H and $R^4$ is selected from H and halogen; and
- wherein for said compound of formula (II)
- X, $Y^1$, $Y^2$ and $Y^3$ are as defined for the compound of formula (I); and
- $R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)
- X is O; and
- $Y^1$ is selected from N and CH; and
- $Y^2$ and $Y^3$ are each CH; and
- $R^1$ is H and $R^2$ is selected from H and C3-C8 alkyl; and
- $R^3$ is H and $R^4$ is selected from H and halogen; and
- wherein for said compound of formula (II)
- X, $Y^1$, $Y^2$ and $Y^3$ are as defined for the compound of formula (I); and
- $R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)
- X is O; and
- $Y^1$ is selected from N and CH; and
- $Y^2$ and $Y^3$ are each CH; and
- $R^1$ is H and $R^2$ is selected from H and C5-C10 cycloalkyl; and
- $R^3$ is H and $R^4$ is selected from H and halogen; and
- wherein for said compound of formula (II)
- X, $Y^1$, $Y^2$ and $Y^3$ are as defined for the compound of formula (I); and
- $R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)
- X is NH; and
- $Y^1$ is selected from N and CH; and
- $Y^2$ and $Y^3$ are each CH; and
- $R^1$ is H and $R^2$ is selected from H and C3-C8 alkyl; and
- $R^3$ is H and $R^4$ is selected from H and halogen; and
- wherein for said compound of formula (II)
- X, $Y^1$, $Y^2$ and $Y^3$ are as defined for the compound of formula (I); and
- $R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)
- X is NH; and
- $Y^1$ is selected from N and CH; and
- $Y^2$ and $Y^3$ are each CH; and
- $R^1$ is H and $R^2$ is selected from H and C5-C10 cycloalkyl; and $R^3$ is H and $R^4$ is selected from H and halogen; and
wherein for said compound of formula (II)
X, $Y^1$, $Y^2$ and $Y^3$ are as defined for the compound of formula (I); and
$R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)
X is selected from O and NH; and
$Y^1$ is selected from N and CH; and
$Y^2$ and $Y^3$ are each CH; and
$R^1$ and $R^2$ are each independently selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and
$R^3$ and $R^4$ are each independently selected from H and F; and
wherein for said compound of formula (II)
X, $y^1$, $Y^2$ and $Y^3$ are as defined for the compound of formula (I); and
$R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)
X is selected from O and NH; and
$Y^1$ is selected from N and CH; and
$Y^2$ and $Y^3$ are each CH; and
$R^1$ is H and $R^2$ is selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and
$R^3$ and $R^4$ are each independently selected from H and F; and
wherein for said compound of formula (II)
X, $Y^1$, $Y^2$ and $Y^3$ are as defined for the compound of formula (I); and
$R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)
X is selected from O and NH; and
$Y^1$ is selected from N and CH; and
$Y^2$ and $Y^3$ are each CH; and
$R^1$ is H and $R^2$ is selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and
$R^3$ is H and $R^4$ is selected from H and F; and
wherein for said compound of formula (II)
X, $Y^1$, $Y^2$ and $Y^3$ are as defined for the compound of formula (I); and
$R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)
X is O; and
$Y^1$ is N; and
$y^2$ and $Y^3$ are each CH; and
$R^1$ and $R^2$ are each independently selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and
$R^3$ is H and $R^4$ is selected from H and F; and
wherein for said compound of formula (II)
X, $Y^1$, $Y^2$ and $Y^3$ are as defined for the compound of formula (I); and
$R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)
X is O; and
$Y^1$, $Y^2$ and $Y^3$ are each CH; and
$R^1$ and $R^2$ are each independently selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and
$R^3$ is H and $R^4$ is selected from H and F; and
wherein for said compound of formula (II)
X, $Y^1$, $Y^2$ and $Y^3$ are as defined for the compound of formula (I); and
$R^{11}$ is equal to $R^1$, $R^{22}$ is equal to $R^2$. $R^{33}$ is equal to $R^3$ and $R^{44}$ is equal to $R^4$ of the compound of formula (I).

In one embodiment, there is provided a process according to the first aspect of the invention, wherein for said compound of formula (I)
X is NH; and
$Y^1$ is N; and
$Y^2$ and $Y^3$ are each CH; and
$R^1$ and $R^2$ are each independently selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and
$R^3$ is H and $R^4$ is selected from H and F; and
wherein for said compound of formula (II)
X, $Y^1$, $Y^2$ and $Y^3$ are as defined for the compound of formula (I); and
$R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)
X is NH; and
$Y^1$, $Y^2$ and $Y^3$ are each CH; and
$R^1$ and $R^2$ are each independently selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and
$R^3$ is H and $R^4$ is selected from H and F; and
wherein for said compound of formula (II)
X, $Y^1$, $Y^2$ and $Y^3$ are as defined for the compound of formula (I); and
$R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)
X is O; and
$Y^1$ is N; and
$Y^2$ and $Y^3$ are each CH; and
$R^1$ is H and $R^2$ is selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and $R^3$ is H and $R^4$ is selected from H and F; and wherein for said compound of formula (II)

X, $Y^1$, $Y^2$ and $Y^3$ are as defined for the compound of formula (I); and $R^{11}$ is equal to $R^1$, $R^{22}$ is equal to $R^2$, $R^{33}$ is equal to $R^3$ and $R^{44}$ is equal to $R^4$ of the compound of formula (I).

In a preferred embodiment, there is provided a process according to the first aspect of the invention, wherein for said compound of formula (I)

X is O; and $Y^1$ is N; and $Y^2$ and $Y^3$ are each CH; and $R^1$ is H and $R^2$ is selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and $R^3$ is H and $R^4$ is H; and wherein for said compound of formula (II)

X, $Y^1$, $Y^2$ and $Y^3$ are as defined for the compound of formula (I); and $R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)

X is O; and $Y^1$, $Y^2$ and $Y^3$ are each CH; and $R^1$ is H and $R^2$ is selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and $R^3$ is H and $R^4$ is selected from H and F; and wherein for said compound of formula (II)

X, $y^1$, $Y^2$ and $Y^3$ are as defined for the compound of formula (I); and $R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)

X is NH; and $Y^1$ is N; and $Y^2$ and $Y^3$ are each CH; and $R^1$ is H and $R^2$ is selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and $R^3$ is H and $R^4$ is selected from H and F; and wherein for said compound of formula (II)

X, $y^1$, $Y^2$ and $Y^3$ are as defined for the compound of formula (I); and $R^{11}$ is equal to $R^1$, $R^{22}$ is equal to $R^2$, $R^{33}$ is equal to $R^3$ and $R^{44}$ is equal to $R^4$ of the compound of formula (I).

In one embodiment, there is provided a process according to the first aspect of the invention, wherein for said compound of formula (I)

X is NH; and $Y^1$, $Y^2$ and $Y^3$ are each CH; and $R^1$ is H and $R^2$ is selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and $R^3$ is H and $R^4$ is selected from H and F; and wherein for said compound of formula (II)

X, $Y^1$, $Y^2$ and $Y^3$ are as defined for the compound of formula (I); and $R^{11}$ is equal to $R^1$, $R^{22}$ is equal to $R^2$, $R^{33}$ is equal to $R^3$ and $R^{44}$ is equal to $R^4$ of the compound of formula (I).

In a preferred embodiment, there is provided a process according to the first aspect of the invention, wherein for said compound of formula (I)

X is selected from O and NH; and $Y^1$, $Y^2$ and $Y^3$ are each selected from N and CH; and $R^1$ is H and $R^2$ is tert-butyl; and $R^3$ and $R^4$ are both H; and wherein for said compound of formula (II)

X, $y^1$, $Y^2$ and $Y^3$ are as defined for the compound of formula (I); and $R^{11}$ is equal to $R^1$, $R^{22}$ is equal to $R^2$, $R^{33}$ is equal to $R^3$ and $R^{44}$ is equal to $R^4$ of the compound of formula (I).

In a preferred embodiment, there is provided a process according to the first aspect of the invention, wherein for said compound of formula (I)

X is selected from O and NH; and $Y^1$ is selected from N and CH; and $Y^2$ and $Y^3$ are each CH; and $R^1$ is H and $R^2$ is tert-butyl; and $R^3$ and $R^4$ are both H; and wherein for said compound of formula (II)

X, $y^1$, $Y^2$ and $Y^3$ are as defined for the compound of formula (I); and $R^{11}$ is equal to $R^1$, $R^{22}$ is equal to $R^2$, $R^{33}$ is equal to $R^3$ and $R^{44}$ is equal to $R^4$ of the compound of formula (I).

In a further preferred embodiment, there is provided a process according to the first aspect of the invention, wherein for said compound of formula (I)

X is selected from O and NH; and $Y^1$ is N; and $Y^2$ and $Y^3$ are each CH; and $R^1$ is H and $R^2$ is tert-butyl; and $R^3$ and $R^4$ are both H; and wherein for said compound of formula (II)

X, $y^1$, $Y^2$ and $Y^3$ are as defined for the compound of formula (I); and $R^{11}$ is equal to $R^1$, $R^{22}$ is equal to $R^2$, $R^{33}$ is equal to $R^3$ and $R^{44}$ is equal to $R^4$ of the compound of formula (I).

In a further preferred embodiment, there is provided a process according to the first aspect of the invention, wherein for said compound of formula (I)

X is selected from O and NH; and $Y^1$, $Y^2$ and $Y^3$ are each CH; and $R^1$ is H and $R^2$ is tert-butyl; and $R^3$ and $R^4$ are both H; and wherein for said compound of formula (II)

X, $y^1$, $Y^2$ and $Y^3$ are as defined for the compound of formula (I); and $R^{11}$ is equal to $R^1$, $R^{22}$ is equal to $R^2$, $R^{33}$ is equal to $R^3$ and $R^{44}$ is equal to $R^4$ of the compound of formula (I).

In a particularly preferred embodiment, there is provided a process according to the first aspect of the invention, wherein said compound of formula (I) is selected from

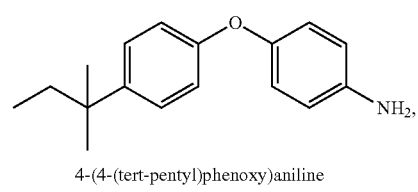

Formula V 4-(4-(tert-pentyl)phenoxy)aniline

Formula VI

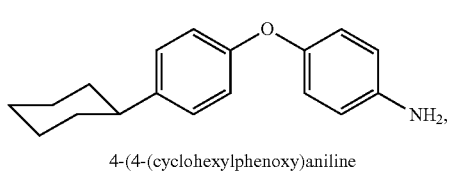

4-(4-(cyclohexylphenoxy)aniline

Formula VII

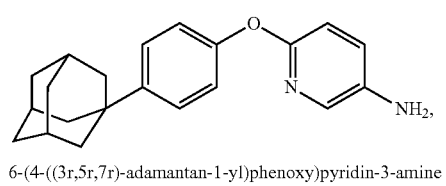

6-(4-((3r,5r,7r)-adamantan-1-yl)phenoxy)pyridin-3-amine

Formula VIII

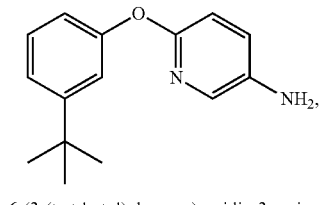

6-(3-(tert-butyl)phenoxy)pyridin-3-amine

Formula IX

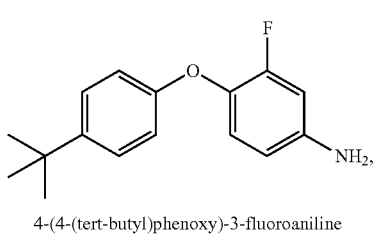

4-(4-(tert-butyl)phenoxy)-3-fluoroaniline

Formula X

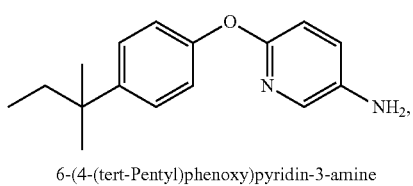

6-(4-(tert-Pentyl)phenoxy)pyridin-3-amine

Formula XI

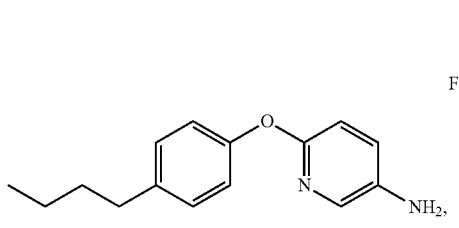

6-(4-Butylphenoxy)pyridin-3-amine

Formula XII

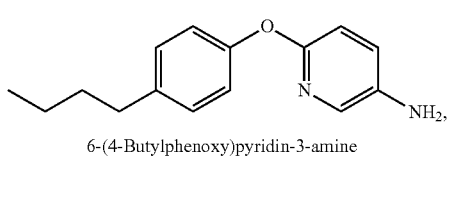

4-(4-(Cyclohexylphenoxy)-3-fluoroaniline

Formula XIII

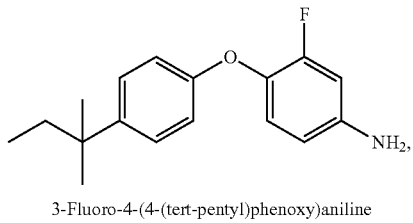

3-Fluoro-4-(4-(tert-pentyl)phenoxy)aniline

Formula XIV

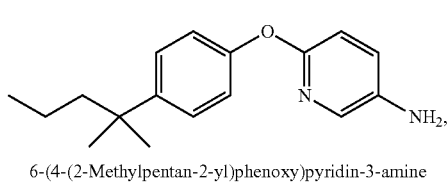

6-(4-(2-Methylpentan-2-yl)phenoxy)pyridin-3-amine

Formula XV

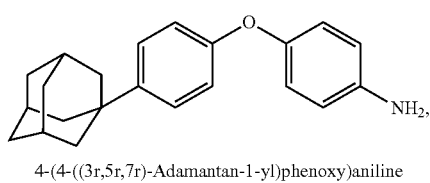

4-(4-((3r,5r,7r)-Adamantan-1-yl)phenoxy)aniline

Formula XVI

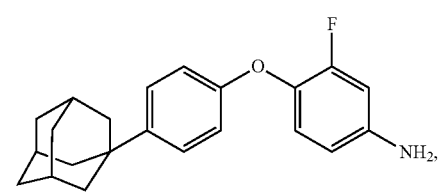

4-(4-((3r,5r,7r)-Adamantan-1-yl)phenoxy)-3-fluoroaniline

Formula XVII

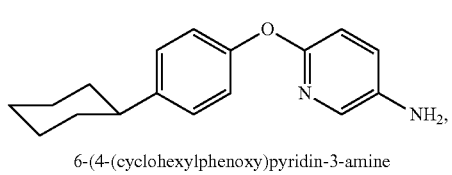

6-(4-(cyclohexylphenoxy)pyridin-3-amine

Formula XVIII

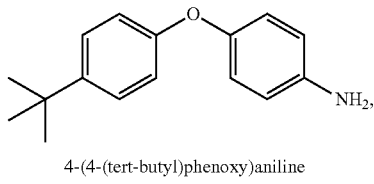

4-(4-(tert-butyl)phenoxy)aniline

Formula XIX

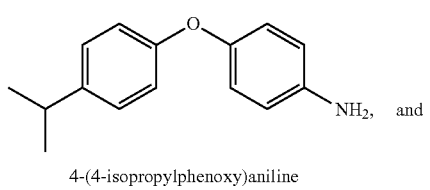  and 4-(4-isopropylphenoxy)aniline

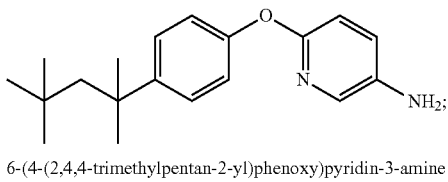

Formula XX 6-(4-(2,4,4-trimethylpentan-2-yl)phenoxy)pyridin-3-amine and wherein said compound of formula (II) is selected from the nitroaryl-analogues of the compounds of formulas (V)-(XX) as shown above.

In a further particularly preferred embodiment, there is provided a process according to the first aspect of the invention,
wherein said compound of formula (I) is 6-(4-(tert-butyl)phenoxy)pyridin-3-amine (formula (Ia)); and
wherein said compound of formula (II) is 2-(4-(tert-butyl)phenoxy)-5-nitropyridine (Formula (IIa)).

Hydrochloride and Monohydrochloride Salts of the Compounds of Formula (I)

The inventors have surprisingly found that, when the compounds of formula (I) are transformed to their hydrochloride salts, stable salts were obtained whereas all attempts to form other acidic addition salts failed. The inventors have further surprisingly found that, when the compounds of formula (I) are transformed to their monohydrochloride salts, the level of purity is further increased in that said monohydrochloride salts are typically obtained as colourless, crystalline solids (see e.g., Example 4), whereas the colour of the respective free base varies from batch to batch (range from colourless to reddish), independent of the analytical level of purity, which is consistently and reproducibly high (99.9% pure as determined by HPLC, Pd-content <1 ppm as determined by elemental analysis). When providing active pharmaceutical ingredients (API's) for the pharmaceutical industry, consistent properties of the API's, including their colour, physical appearance, purity, solubility and reproducibility of manufacture are of utmost importance. Accordingly, the high purity, colourless and crystalline monohydrochloride salts of the compounds of formula (I) are particularly useful as API's, which have been found highly consistent in repeated multi-kg large scale manufacture.

Figure 6:
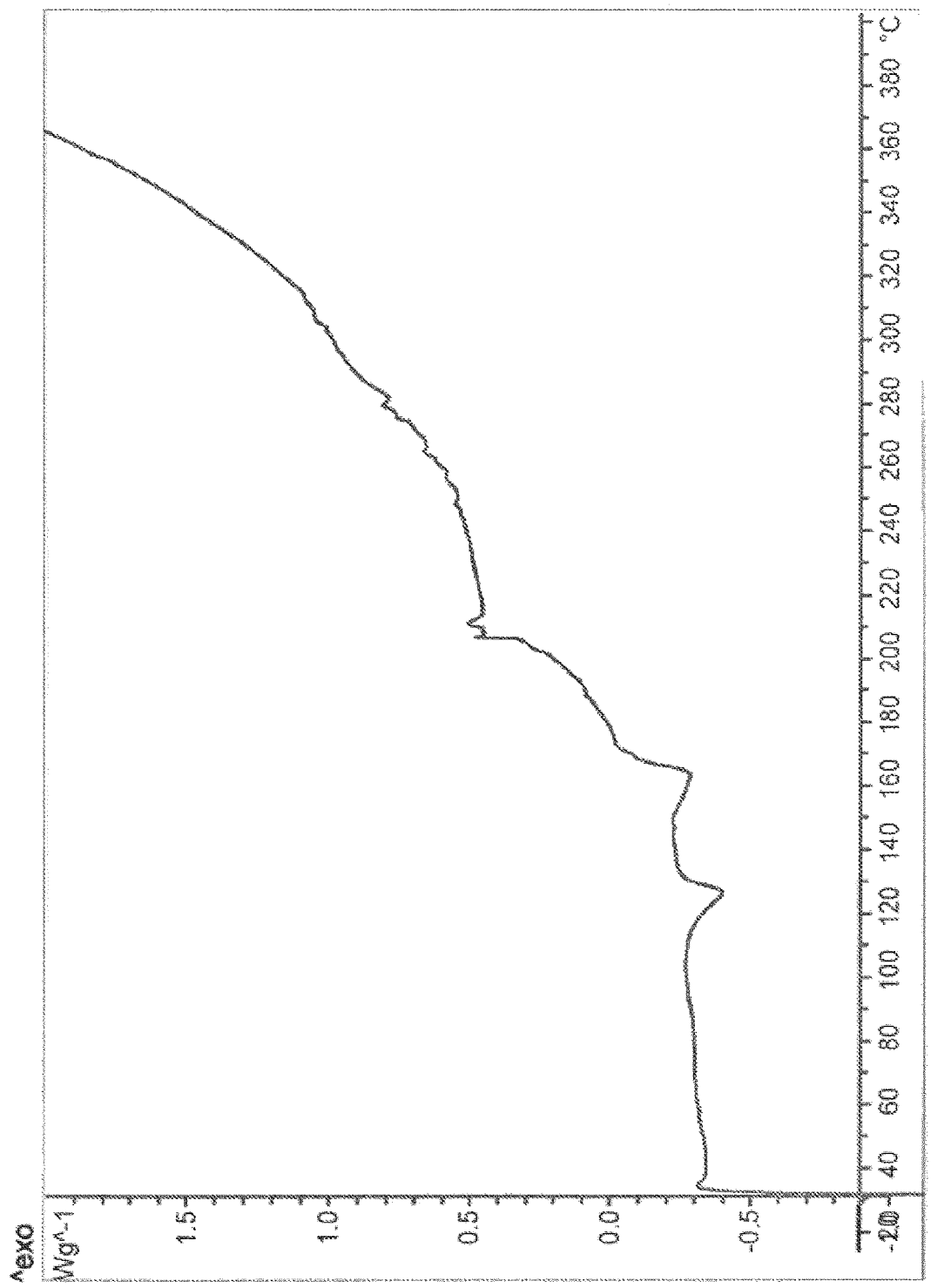
FIG. 6 shows a DSC thermogram of a substance that was obtained when reacting 6-(4-(tert-butyl)phenoxy)pyridin-3-amine (formula (Ia)) with more than 1.5 molar equivalents of hydrochloric acid (Example 5). The DSC thermogram indicates that the substance has no sharp melting point and suggests that at least two species are present.

Further surprisingly, attempts at forming other acid addition salts or the respective dihydrochloride salts failed (see Example 5). For example, when more than 1.5 molar quivalents of hydrochloric acid were used to form a hydrochloride salt of the compound of formula (I), a mixture of mono- and dichloride salts with unsharp melting points was obtained (see Example 5 and FIG. 6).

Thus, in one embodiment, there is provided a process according to the first aspect of the invention, further comprising reacting the compound of formula (I) or (Ia) with hydrochloric acid, usually with equal or more than about 1.5 molar equivalents of hydrochloric acid, preferably with equal or more than about 1.5 molar equivalents and less than about 5 molar equivalents of hydrochloric acid, more preferably with equal or more than about 2 molar equivalents and less than about 3 molar equivalents of hydrochloric acid, even more preferably with about 2.5 molar equivalents of hydrochloric acid to form a hydrochloride salt of said compound of formula (I) or (Ia).

Thus, in one embodiment, there is provided a process according to the first aspect of the invention, further comprising reacting the compound of formula (I) or (Ia) with less than about 1.5 molar equivalents of hydrochloric acid, usually with less than about 1.5 and equal or more than about 1 molar equivalents of hydrochloric acid, preferably about 1.4 molar equivalents, more preferably about 1.3 molar equivalents, yet more preferably about 1.2 molar equivalents, even more preferably about 1.1 molar equivalents, most preferably about 1 molar equivalent, e.g., about 1.01 molar equivalents of hydrochloric acid, to form the monohydrochloride salt of said compound of formula (I) or (Ia).

In a preferred embodiment, there is provided a process according to the first aspect of the invention, further comprising reacting the compound of formula (I) or (Ia) with less than about 1.5 molar equivalents of hydrochloric acid, usually with less than about 1.5 and equal or more than about 1 molar equivalents of hydrochloric acid, preferably about 1.4 molar equivalents, more preferably about 1.3 molar equivalents, yet more preferably about 1.2 molar equivalents, even more preferably about 1.1 molar equivalents, most preferably about 1 molar equivalent, e.g., about 1.01 molar equivalents of hydrochloric acid, to form the monohydrochloride salt of said compound of formula (I) or (Ia); wherein said reacting the compound of formula (I) or (Ia) with hydrochloric acid is performed in a protic solvent, preferably in 2-propanol.

In one embodiment, there is provided a process according to the first aspect of the invention, further comprising reacting the compound of formula (I) or (Ia) with less than about 1.5 molar equivalents of hydrochloric acid, usually with less than about 1.5 and equal or more than about 1 molar equivalents of hydrochloric acid, preferably about 1.4 molar equivalents, more preferably about 1.3 molar equivalents, yet more preferably about 1.2 molar equivalents, even more preferably about 1.1 molar equivalents, most preferably about 1 molar equivalent, e.g., about 1.01 molar equivalents of hydrochloric acid, to form the monohydrochloride salt of said compound of formula (I) or (Ia), followed by crystallizing said monohydrochloride salt. In one embodiment, there is provided a process according to the first aspect of the invention, further comprising reacting the compound of formula (I) or (Ia) with less than about 1.5 molar equivalents of hydrochloric acid, usually with less than about 1.5 and equal or more than about 1 molar equivalents of hydrochloric acid, preferably about 1.4 molar equivalents, more preferably about 1.3 molar equivalents, yet more preferably about 1.2 molar equivalents, even more preferably about 1.1 molar equivalents, most preferably about 1 molar equivalent, e.g., about 1.01 molar equivalents of hydrochloric acid, to form the monohydrochloride salt of said compound of formula (I) or (Ia), followed by crystallizing said monohydrochloride salt, wherein said crystallizing comprises precipitating said monohydrochloride salt in crystalline form from a solvent mixture comprising a protic solvent and a non-polar solvent, most preferably from a solvent mixture comprising 2-propanol and heptane.

In one embodiment, there is provided a process according to the first aspect of the invention, further comprising crystallizing the compound of formula (I) or (Ia) and reacting the compound of formula (I) or (Ia) with less than about 1.5 molar equivalents of hydrochloric acid, usually with less than about 1.5 and equal or more than about 1 molar equivalents of hydrochloric acid, preferably about 1.4 molar equivalents, more preferably about 1.3 molar equivalents, yet more preferably about 1.2 molar equivalents, even more preferably about 1.1 molar equivalents, most preferably about 1 molar equivalent, e.g., about 1.01 molar equivalents of hydrochloric acid, to form the monohydrochloride salt of said compound of formula (I) or (Ia).

In one embodiment, there is provided a process according to the first aspect of the invention, further comprising contacting the compound of formula (I) or (Ia) with activated charcoal; crystallizing the compound of formula (I) or (Ia); and reacting the compound of formula (I) or (Ia) with less than about 1.5 molar equivalents of hydrochloric acid, usually with less than about 1.5 and equal or more than about 1 molar equivalents of hydrochloric acid, preferably about 1.4 molar equivalents, more preferably about 1.3 molar equivalents, yet more preferably about 1.2 molar equivalents, even more preferably about 1.1 molar equivalents, most preferably about 1 molar equivalent, e.g., about 1.01 molar equivalents of hydrochloric acid, to form the monohydrochloride salt of said compound of formula (I) or (Ia).

In one embodiment, there is provided a process according to the first aspect of the invention, further comprising contacting the compound of formula (I) or (Ia) with activated charcoal; crystallizing the compound of formula (I) or (Ia); and reacting the compound of formula (I) or (Ia) with less than about 1.5 molar equivalents of hydrochloric acid, usually with less than about 1.5 and equal or more than about 1 molar equivalents of hydrochloric acid, preferably about 1.4 molar equivalents, more preferably about 1.3 molar equivalents, yet more preferably about 1.2 molar equivalents, even more preferably about 1.1 molar equivalents, most preferably about 1 molar equivalent, e.g., about 1.01 molar equivalents of hydrochloric acid, to form the monohydrochloride salt of said compound of formula (I) or (Ia); wherein said crystallizing comprises precipitating said compound of formula (I) or (Ia) in crystalline form from a solvent mixture comprising a protic solvent and a non-polar solvent, most preferably from a solvent mixture comprising 2-propanol and heptane.

In one embodiment, there is provided a process according to the first aspect of the invention, further comprising crystallizing the compound of formula (I) or (Ia) and reacting the compound of formula (I) or (Ia) with less than about 1.5 molar equivalents of hydrochloric acid, usually with less than about 1.5 and equal or more than about 1 molar equivalents of hydrochloric acid, preferably about 1.4 molar equivalents, more preferably about 1.3 molar equivalents, yet more preferably about 1.2 molar equivalents, even more preferably about 1.1 molar equivalents, most preferably about 1 molar equivalent, e.g., about 1.01 molar equivalents of hydrochloric acid, to form the monohydrochloride salt of said compound of formula (I) or (Ia), followed by crystallizing said monohydrochloride salt.

In a second aspect, the present invention provides a process for making a hydrochloride salt of the compound of formula (I)

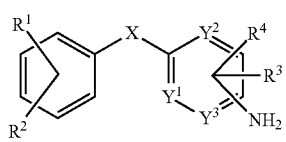

Formula (I)

wherein X is selected from O and NH; and
wherein $Y^1$, $Y^2$ and $Y^3$ are each independently selected from N and CH; and
wherein $R^1$ and $R^2$ are each independently selected from H, C1-C10 alkyl and C3-C12 cycloalkyl; and
wherein $R^3$ and $R^4$ are each independently selected from H, halogen and C1-C10 alkyl comprising reacting the compound of formula (I) with hydrochloric acid, usually with equal or more than about 1.5 molar equivalents of hydrochloric acid, preferably with equal or more than about 1.5 molar equivalents and less than about 5 molar equivalents of hydrochloric acid, more preferably with equal or more than about 2 molar equivalents and less than about 3 molar equivalents of hydrochloric acid, even more preferably with about 2.5 molar equivalents of hydrochloric acid to form a hydrochloride salt of said compound of formula (I).

In a third aspect, the present invention provides a process for making a monohydrochloride salt of the compound of formula (I)

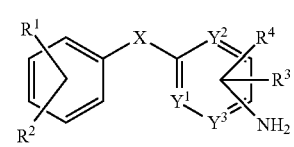

Formula (I)

wherein X is selected from O and NH; and
wherein $Y^1$, $Y^2$ and $Y^3$ are each independently selected from N and CH; and
wherein $R^1$ and $R^2$ are each independently selected from H, C1-C10 alkyl and C3-C12 cycloalkyl; and
wherein $R^3$ and $R^4$ are each independently selected from H, halogen and C1-C10 alkyl comprising reacting said compound of formula (I) with less than 1.5 molar equivalents of hydrochloric acid, usually with less than about 1.5 and equal or more than about 1 molar equivalents of hydrochloric acid, preferably about 1.4 molar equivalents, more preferably about 1.3 molar equivalents, yet more preferably about 1.2 molar equivalents, even more preferably about 1.1 molar equivalents, most preferably about 1 molar equivalent, e.g., about 1.01 molar equivalents of hydrochloric acid, to form the monohydrochloride salt of the compound of formula (I).

In one embodiment, there is provided a process according to the third aspect of the invention, further comprising crystallizing said monohydrochloride salt of the compound of formula (I).

In a preferred embodiment, there is provided a process according to the third aspect of the invention, further comprising crystallizing said monohydrochloride salt of the compound of formula (I), wherein said crystallizing comprises precipitating said monohydrochloride salt in crystalline form from a solvent mixture comprising a protic solvent and a non-polar solvent, most preferably from a solvent mixture comprising 2-propanol and heptane.

In one embodiment, there is provided a process according to the third aspect of the invention, wherein the compound of formula (I) is crystallized prior to reacting it with hydrochloric acid.

In one embodiment, there is provided a process according to the third aspect of the invention, wherein the compound of formula (I) is contacted with activated charcoal and crystallized prior to reacting it with hydrochloric acid.

In one embodiment, there is provided a process according to the third aspect of the invention, wherein the compound of formula (I) is contacted with activated charcoal and crystallized by precipitating it in crystalline form from a solvent mixture comprising a protic solvent and a non-polar solvent, most preferably from a solvent mixture comprising 2-propanol and heptane, prior to reacting it with hydrochloric acid.

In one embodiment, there is provided a process according to the third aspect of the invention, further comprising crystallizing said monohydrochloride salt of the compound of formula (VI); wherein the compound of formula (I) is crystallized prior to reacting it with hydrochloric acid.

In one embodiment, there is provided a process according to the third aspect of the invention, further comprising crystallizing said monohydrochloride salt of the compound of formula (I); wherein the compound of formula (I) is contacted with carbon on activated charcoal and crystallized prior to reacting it with hydrochloric acid.

In a preferred embodiment, there is provided a process according to the third aspect of the invention, wherein said reacting the compound of formula (I) with hydrochloric acid is performed in a protic solvent, preferably in 2-propanol.

Figure 2:
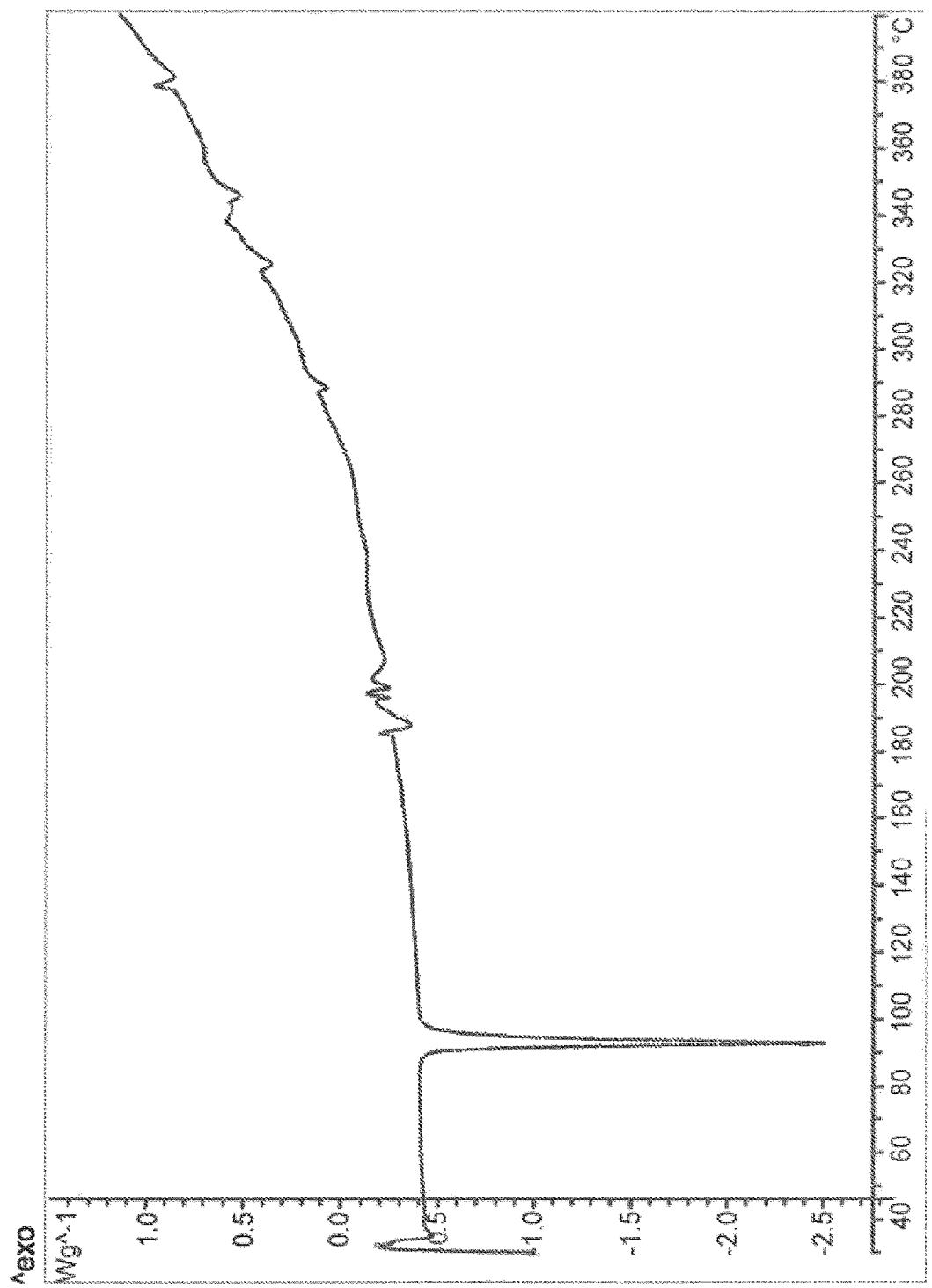
FIG. 2 shows a DSC thermogram of the compound of formula (Ia), i.e. 6-(4-(tert-butyl)phenoxy)pyridin-3-amine. The DSC thermogram indicates a melting point of the compound of formula (Ia) with an onset of 90.8° C. and peaking at 92.0° C.

It has further surprisingly been found that monohydrochloride salts of the compounds of formula (I) have improved properties, such as higher melting points and improved solubilities in aqueous media, as compared to the compounds of formula (I) in their free base form. For example, 6-(4-(tert-butyl)phenoxy)pyridin-3-amine monohydrochloride has a melting point of 173° C. (measured by DSC; see FIG. 1), whereas the respective free base of formula (Ia) has a melting point of only 92° C. (measured by DSC; see FIG. 2). Surprisingly, all attempts at forming other acid addition salts failed (Example 5). In addition, attempts at forming the respective dihydrochloride salt of the compound of formula (Ia) surprisingly resulted in the formation of a substance (Example 5) having two melting points (FIG. 6), suggesting that at least two species were present.

In a fourth aspect, the present invention provides a hydrochloride salt of the compound of formula (I)

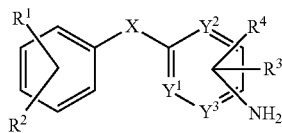

Formula (I)

wherein X is selected from O and NH; and wherein $Y^1$, $Y^2$ and $Y^3$ are each independently selected from N and CH; and wherein $R^1$ and $R^2$ are each independently selected from H, C1-C10 alkyl and C3-C12 cycloalkyl and wherein $R^3$ and $R^4$ are each independently selected from H, halogen and C1-C10 alkyl.

In a fifth aspect, the present invention provides a monohydrochloride salt of the compound of formula (I)

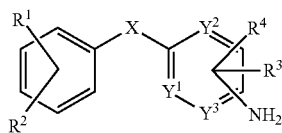

Formula (I)

wherein X is selected from O and NH; and wherein $Y^1$, $Y^2$ and $Y^3$ are each independently selected from N and CH; and wherein $R^1$ and $R^2$ are each independently selected from H, C1-C10 alkyl and C3-C12 cycloalkyl and wherein $R^3$ and $R^4$ are each independently selected from H, halogen and C1-C10 alkyl.

In a preferred embodiment, there is provided a process according to the second and third aspect of the invention or a hydrochloride salt and a monohydrochloride salt according to the fourth and fifth aspect of the invention, wherein for said compound of formula (I) X is selected from O and NH.

In a particularly preferred embodiment, there is provided a process according to the second and third aspect of the invention or a hydrochloride salt and a monohydrochloride salt according to the fourth and fifth aspect of the invention, wherein for said compound of formula (I) X is O.

In a further embodiment, there is provided a process according to the second and third aspect of the invention or a hydrochloride salt and a monohydrochloride salt according to the fourth and fifth aspect of the invention, wherein for said compound of formula (I) $Y^1$, $Y^2$ and $Y^3$ are each selected from N and CH, wherein at least one of $Y^1$, $Y^2$ and $Y^3$ is CH.

In a further embodiment, there is provided a process according to the second and third aspect of the invention or a hydrochloride salt and a monohydrochloride salt according to the fourth and fifth aspect of the invention, wherein for said compound of formula (I) $Y^1$, $Y^2$ and $Y^3$ are each selected from N and CH, wherein at least one of $Y^1$ and $Y^3$ is CH.

In one embodiment, there is provided a process according to the second and third aspect of the invention or a hydrochloride salt and a monohydrochloride salt according to the fourth and fifth aspect of the invention, wherein for said compound of formula (I) $Y^1$ is selected from N and CH; and $Y^2$ and $Y^3$ are each CH.

In a preferred embodiment, there is provided a process according to the second and third aspect of the invention or a hydrochloride salt and a monohydrochloride salt according to the fourth and fifth aspect of the invention, wherein for said compound of formula (I) $Y^1$ is N; and $Y^2$ and $Y^3$ are each CH.

In a further preferred embodiment, there is provided a process according to the second and third aspect of the invention or a hydrochloride salt and a monohydrochloride salt according to the fourth and fifth aspect of the invention, wherein for said compound of formula (I) each of $Y^1$, $Y^2$ and $Y^3$ are CH.

In one embodiment, there is provided a process according to the second and third aspect of the invention or a hydrochloride salt and a monohydrochloride salt according to the fourth and fifth aspect of the invention, wherein for said compound of formula (I) $Y^1$ and $Y^2$ are both CH; and $Y^3$ is N.

In one embodiment, there is provided a process according to the second and third aspect of the invention or a hydrochloride salt and a monohydrochloride salt according to the fourth and fifth aspect of the invention, wherein for said compound of formula (I) $Y^1$ and $Y^2$ are both N; and $Y^3$ is CH.

In one embodiment, there is provided a process according to the second and third aspect of the invention or a hydrochloride salt and a monohydrochloride salt according to the fourth and fifth aspect of the invention, wherein for said compound of formula (I) $R^1$ and $R^2$ are each independently selected from H and C1-C10 alkyl.

In a further embodiment, there is provided a process according to the second and third aspect of the invention or a hydrochloride salt and a monohydrochloride salt according to the fourth and fifth aspect of the invention, wherein for said compound of formula (I) $R^1$ and $R^2$ are each independently selected from H and C3-C12 cycloalkyl.

In a preferred embodiment, there is provided a process according to the second and third aspect of the invention or a hydrochloride salt and a monohydrochloride salt according to the fourth and fifth aspect of the invention, wherein for said compound of formula (I) $R^1$ is H and $R^2$ is selected from H, C1-C10 alkyl and C3-C12 cycloalkyl.

In a further preferred embodiment, there is provided a process according to the second and third aspect of the invention or a hydrochloride salt and a monohydrochloride salt according to the fourth and fifth aspect of the invention, wherein for said compound of formula (I) $R^1$ is H and $R^2$ is selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl.

In a particularly preferred embodiment, there is provided a process according to the second and third aspect of the invention or a hydrochloride salt and a monohydrochloride salt according to the fourth and fifth aspect of the invention, wherein for said compound of formula (I) $R^1$ is H and $R^2$ is tert-butyl.

In one embodiment, there is provided a process according to the second and third aspect of the invention or a hydrochloride salt and a monohydrochloride salt according to the fourth and fifth aspect of the invention, wherein for said compound of formula (I) $R^3$ and $R^4$ are each independently selected from H, and halogen.

In one embodiment, there is provided a process according to the second and third aspect of the invention or a hydrochloride salt and a monohydrochloride salt according to the fourth and fifth aspect of the invention, wherein for said compound of formula (I) $R^3$ and $R^4$ are both halogen, preferably fluorine.

In a preferred embodiment, there is provided a process according to the second and third aspect of the invention or a hydrochloride salt and a monohydrochloride salt according to the fourth and fifth aspect of the invention, wherein for said compound of formula (I) $R^3$ is H and $R^4$ is selected from H, and halogen, preferably from H and fluorine.

In a particularly preferred embodiment, there is provided a process according to the second and third aspect of the invention or a hydrochloride salt and a monohydrochloride salt according to the fourth and fifth aspect of the invention, wherein for said compound of formula (I) $R^3$ and $R^4$ are both H.

In one embodiment, there is provided a process according to the second and third aspect of the invention or a hydrochloride salt and a monohydrochloride salt according to the fourth and fifth aspect of the invention, wherein for said compound of formula (I)
  X is selected from O and NH; and
  $Y^1$, $Y^2$ and $Y^3$ are each selected from N and CH, wherein at least one of $Y^1$, $Y^2$ and $Y^3$ is CH; and
  $R^1$ and $R^2$ are each independently selected from H, C1-C10 alkyl and C3-C12 cycloalkyl; and
  $R^3$ and $R^4$ are each independently selected from H and halogen.

In one embodiment, there is provided a process according to the second and third aspect of the invention or a hydrochloride salt and a monohydrochloride salt according to the fourth and fifth aspect of the invention, wherein for said compound of formula (I)
  X is selected from O and NH; and
  $Y^1$, $Y^2$ and $Y^3$ are each selected from N and CH, wherein at least one of $Y^1$ and $Y^3$ is CH; and
  $R^1$ and $R^2$ are each independently selected from H, C1-C10 alkyl and C3-C12 cycloalkyl; and
  $R^3$ and $R^4$ are each independently selected from H and halogen.

In one embodiment, there is provided a process according to the second and third aspect of the invention or a hydrochloride salt and a monohydrochloride salt according to the fourth and fifth aspect of the invention, wherein for said compound of formula (I)
  X is selected from O and NH; and
  $Y^1$ is selected from N and CH; and
  $Y^2$ and $Y^3$ are each CH; and
  $R^1$ and $R^2$ are each independently selected from H, C1-C10 alkyl and C3-C12 cycloalkyl; and
  $R^3$ and $R^4$ are each independently selected from H and halogen.

In one embodiment, there is provided a process according to the second and third aspect of the invention or a hydrochloride salt and a monohydrochloride salt according to the fourth and fifth aspect of the invention, wherein for said compound of formula (I)
  X is selected from O and NH; and
  $Y^1$ is selected from N and CH; and
  $Y^2$ and $Y^3$ are each CH; and
  $R^1$ is H and $R^2$ is selected from H, C1-C10 alkyl and C3-C12 cycloalkyl; and
  $R^3$ and $R^4$ are each independently selected from H and halogen.

In one embodiment, there is provided a process according to the second and third aspect of the invention or a hydrochloride salt and a monohydrochloride salt according to the fourth and fifth aspect of the invention, wherein for said compound of formula (I)
  X is selected from O and NH; and
  $Y^1$ is selected from N and CH; and
  $Y^2$ and $Y^3$ are each CH; and
  $R^1$ is H and $R^2$ is selected from H, C1-C10 alkyl and C3-C12 cycloalkyl; and
  $R^3$ is H and $R^4$ is selected from H and halogen.

In one embodiment, there is provided a process according to the second and third aspect of the invention or a hydrochloride salt and a monohydrochloride salt according to the fourth and fifth aspect of the invention, wherein for said compound of formula (I)
  X is selected from O and NH; and
  $Y^1$ is selected from N and CH; and
  $Y^2$ and $Y^3$ are each CH; and
  $R^1$ is H and $R^2$ is selected from H, C3-C8 alkyl and 05-C10 cycloalkyl; and
  $R^3$ is H and $R^4$ is selected from H and halogen.

In one embodiment, there is provided a process according to the second and third aspect of the invention or a hydrochloride salt and a monohydrochloride salt according to the fourth and fifth aspect of the invention, wherein for said compound of formula (I)
  X is selected from O and NH; and
  $Y^1$ is selected from N and CH; and
  $Y^2$ and $Y^3$ are each CH; and
  $R^1$ is H and $R^2$ is selected from H and C3-C8 alkyl; and
  $R^3$ is H and $R^4$ is selected from H and halogen.

In one embodiment, there is provided a process according to the second and third aspect of the invention or a hydrochloride salt and a monohydrochloride salt according to the fourth and fifth aspect of the invention, wherein for said compound of formula (I)
X is selected from O and NH; and
$Y^1$ is selected from N and CH; and
$Y^2$ and $Y^3$ are each CH; and
$R^1$ is H and $R^2$ is selected from H and C5-C10 cycloalkyl; and
$R^3$ is H and $R^4$ is selected from H and halogen.

In one embodiment, there is provided a process according to the second and third aspect of the invention or a hydrochloride salt and a monohydrochloride salt according to the fourth and fifth aspect of the invention, wherein for said compound of formula (I)
X is O; and
$Y^1$ is selected from N and CH; and
$Y^2$ and $Y^3$ are each CH; and
$R^1$ is H and $R^2$ is selected from H and C3-08 alkyl; and
$R^3$ is H and $R^4$ is selected from H and halogen.

In one embodiment, there is provided a process according to the second and third aspect of the invention or a hydrochloride salt and a monohydrochloride salt according to the fourth and fifth aspect of the invention, wherein for said compound of formula (I)
X is O; and
$Y^1$ is selected from N and CH; and
$Y^2$ and $Y^3$ are each CH; and
$R^1$ is H and $R^2$ is selected from H and C5-C10 cycloalkyl; and
$R^3$ is H and $R^4$ is selected from H and halogen.

In one embodiment, there is provided a process according to the second and third aspect of the invention or a hydrochloride salt and a monohydrochloride salt according to the fourth and fifth aspect of the invention, wherein for said compound of formula (I)
X is NH; and
$Y^1$ is selected from N and CH; and
$Y^2$ and $Y^3$ are each CH; and
$R^1$ is H and $R^2$ is selected from H and C3-C8 alkyl; and
$R^3$ is H and $R^4$ is selected from H and halogen.

In one embodiment, there is provided a process according to the second and third aspect of the invention or a hydrochloride salt and a monohydrochloride salt according to the fourth and fifth aspect of the invention, wherein for said compound of formula (I)
X is NH; and
$Y^1$ is selected from N and CH; and
$Y^2$ and $Y^3$ are each CH; and
$R^1$ is H and $R^2$ is selected from H and C5-C10 cycloalkyl; and
$R^3$ is H and $R^4$ is selected from H and halogen.

In one embodiment, there is provided a process according to the second and third aspect of the invention or a hydrochloride salt and a monohydrochloride salt according to the fourth and fifth aspect of the invention, wherein for said compound of formula (I)
X is selected from O and NH; and
$Y^1$ is selected from N and CH; and
$Y^2$ and $Y^3$ are each CH; and
$R^1$ and $R^2$ are each independently selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and
$R^{12}$ and $R^{13}$ are each independently selected from H and F.

In one embodiment, there is provided a process according to the second and third aspect of the invention or a hydrochloride salt and a monohydrochloride salt according to the fourth and fifth aspect of the invention, wherein for said compound of formula (I)
X is selected from O and NH; and
$Y^1$ is selected from N and CH; and
$Y^2$ and $Y^3$ are each CH; and
$R^1$ is H and $R^2$ is selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and
$R^3$ and $R^4$ are each independently selected from H and F.

In one embodiment, there is provided a process according to the second and third aspect of the invention or a hydrochloride salt and a monohydrochloride salt according to the fourth and fifth aspect of the invention, wherein for said compound of formula (I)
X is selected from O and NH; and
$Y^1$ is selected from N and CH; and
$Y^2$ and $Y^3$ are each CH; and
$R^1$ is H and $R^2$ is selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and
$R^3$ is H and $R^4$ is selected from H and F.

In one embodiment, there is provided a process according to the second and third aspect of the invention or a hydrochloride salt and a monohydrochloride salt according to the fourth and fifth aspect of the invention, wherein for said compound of formula (I)
X is O; and
$Y^1$ is N; and
$Y^2$ and $Y^3$ are each CH; and
$R^1$ and $R^2$ are each independently selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and
$R^3$ is H and $R^4$ is selected from H and F.

In one embodiment, there is provided a process according to the second and third aspect of the invention or a hydrochloride salt and a monohydrochloride salt according to the fourth and fifth aspect of the invention, wherein for said compound of formula (I)
X is O; and
$Y^1$, $Y^2$ and $Y^3$ are each CH; and
$R^1$ and $R^2$ are each independently selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and
$R^3$ is H and $R^4$ is selected from H and F.

In one embodiment, there is provided a process according to the second and third aspect of the invention or a hydrochloride salt and a monohydrochloride salt according to the fourth and fifth aspect of the invention, wherein for said compound of formula (I)
X is NH; and
$Y^1$ is N; and
$Y^2$ and $Y^3$ are each CH; and
$R^1$ and $R^2$ are each independently selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and $R^3$ is H and $R^4$ is selected from H and F.

In one embodiment, there is provided a process according to the second and third aspect of the invention or a hydrochloride salt and a monohydrochloride salt according to the fourth and fifth aspect of the invention, wherein for said compound of formula (I)

X is NH; and
$Y^1$, $Y^2$ and $Y^3$ are each CH; and
$R^1$ and $R^2$ are each independently selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and
$R^3$ is H and $R^4$ is selected from H and F.

In one embodiment, there is provided a process according to the second and third aspect of the invention or a hydrochloride salt and a monohydrochloride salt according to the fourth and fifth aspect of the invention, wherein for said compound of formula (I)

X is O; and
$Y^1$ is N; and
$Y^2$ and $Y^3$ are each CH; and
$R^1$ is H and $R^2$ is selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and
$R^3$ is H and $R^4$ is selected from H and F.

In a preferred embodiment, there is provided a process according to the second and third aspect of the invention or a hydrochloride salt and a monohydrochloride salt according to the fourth and fifth aspect of the invention, wherein for said compound of formula (I)

X is O; and
$Y^1$ is N; and
$Y^2$ and $Y^3$ are each CH; and
$R^1$ is H and $R^2$ is selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and
$R^3$ is H and $R^4$ is H.

In one embodiment, there is provided a process according to the second and third aspect of the invention or a hydrochloride salt and a monohydrochloride salt according to the fourth and fifth aspect of the invention, wherein for said compound of formula (I)

X is O; and
$Y^1$, $Y^2$ and $Y^3$ are each CH; and
$R^1$ is H and $R^2$ is selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and
$R^3$ is H and $R^4$ is selected from H and F.

In one embodiment, there is provided a process according to the second and third aspect of the invention or a hydrochloride salt and a monohydrochloride salt according to the fourth and fifth aspect of the invention, wherein for said compound of formula (I)

X is NH; and
$Y^1$ is N; and
$Y^2$ and $Y^3$ are each CH; and
$R^1$ is H and $R^2$ is selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and
$R^3$ is H and $R^4$ is selected from H and F.

In one embodiment, there is provided a process according to the second and third aspect of the invention or a hydrochloride salt and a monohydrochloride salt according to the fourth and fifth aspect of the invention, wherein for said compound of formula (I)

X is NH; and
$Y^1$, $Y^2$ and $Y^3$ are each CH; and
$R^1$ is H and $R^2$ is selected from H, methyl, ethyl, n-propyl, iso-propyl, n-butyl, sec-butyl, tert-butyl, 1,1-dimethylpropyl, 1,1-dimethyl-3,3-dimethylbutyl, 1,1-dimethylbutyl, cyclohexyl and adamantyl; and
$R^3$ is H and $R^4$ is selected from H and F.

In a preferred embodiment, there is provided a process according to the second and third aspect of the invention or a hydrochloride salt and a monohydrochloride salt according to the fourth and fifth aspect of the invention, wherein for said compound of formula (I)

X is selected from O and NH; and
$Y^1$, $Y^2$ and $Y^3$ are each selected from N and CH; and
$R^1$ is H and $R^2$ is tert-butyl; and
$R^3$ and $R^4$ are both H.

In a further preferred embodiment, there is provided a process according to the second and third aspect of the invention or a hydrochloride salt and a monohydrochloride salt according to the fourth and fifth aspect of the invention, wherein for said compound of formula (I)

X is selected from O and NH; and
$Y^1$ is selected from N and CH; and
$Y^2$ and $Y^3$ are each CH; and
$R^1$ is H and $R^2$ is tert-butyl; and
$R^3$ and $R^4$ are both H.

In a further preferred embodiment, there is provided a process according to the second and third aspect of the invention or a hydrochloride salt and a monohydrochloride salt according to the fourth and fifth aspect of the invention, wherein for said compound of formula (I)

X is selected from O and NH; and
$Y^1$ is N; and
$Y^2$ and $Y^3$ are each CH; and
$R^1$ is H and $R^2$ is tert-butyl; and
$R^3$ and $R^4$ are both H.

In a further preferred embodiment, there is provided a process according to the second and third aspect of the invention or a hydrochloride salt and a monohydrochloride salt according to the fourth and fifth aspect of the invention, wherein for said compound of formula (I)

X is selected from O and NH; and
$Y^1$, $Y^2$ and $Y^3$ are each CH; and
$R^1$ is H and $R^2$ is tert-butyl; and
$R^3$ and $R^4$ are both H.

In a particularly preferred embodiment, there is provided a process according to the second and third aspect of the invention or a hydrochloride salt and a monohydrochloride salt according to the fourth and fifth aspect of the invention, wherein said compound of formula (I) is selected from

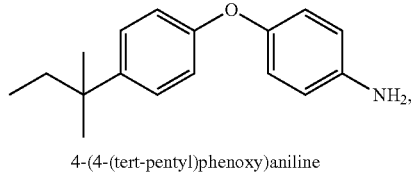

Formula V 4-(4-(tert-pentyl)phenoxy)aniline

Formula VI

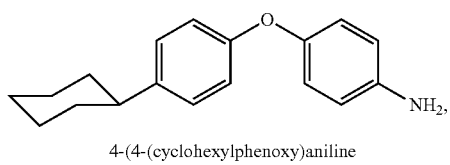

4-(4-(cyclohexylphenoxy)aniline

Formula VII

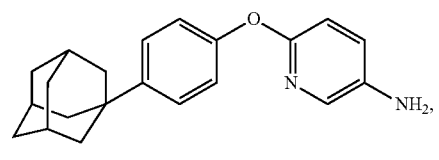

6-(4-((3r,5r,7r)-adamantan-1-yl)phenoxy)pyridin-3-amine

Formula VIII

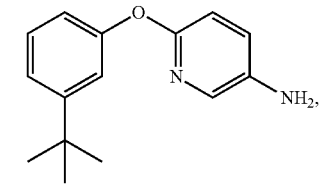

6-(3-(tert-butyl)phenoxy)pyridin-3-amine

Formula IX

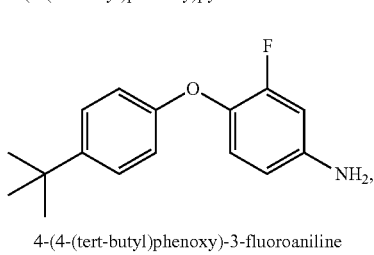

4-(4-(tert-butyl)phenoxy)-3-fluoroaniline

Formula X

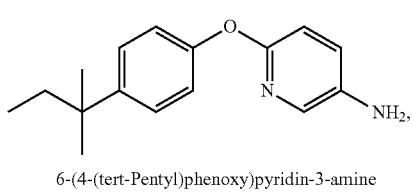

6-(4-(tert-Pentyl)phenoxy)pyridin-3-amine

Formula XI

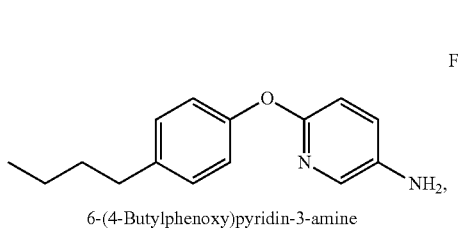

6-(4-Butylphenoxy)pyridin-3-amine

Formula XII

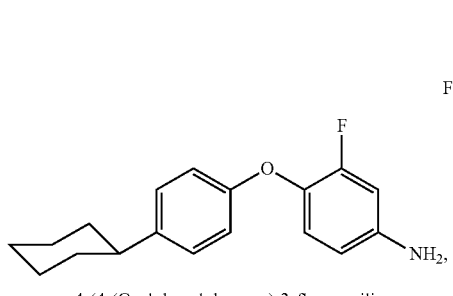

4-(4-(Cyclohexylphenoxy)-3-fluoroaniline

Formula XIII

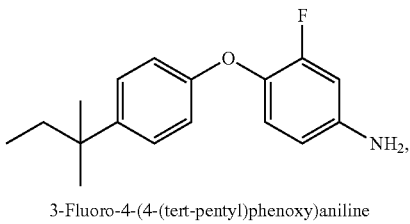

3-Fluoro-4-(4-(tert-pentyl)phenoxy)aniline

Formula XIV

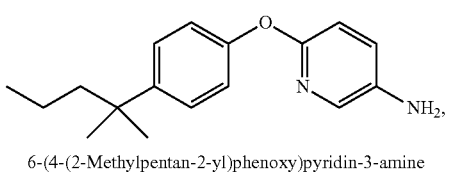

6-(4-(2-Methylpentan-2-yl)phenoxy)pyridin-3-amine

Formula XV

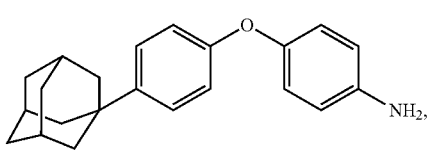

4-(4-((3r,5r,7r)-Adamantan-1-yl)phenoxy)aniline

Formula XVI

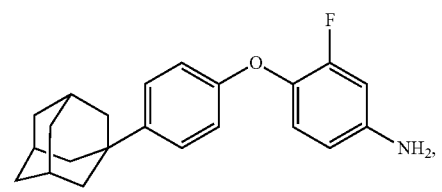

4-(4-((3r,5r,7r)-Adamantan-1-yl)phenoxy)-3-fluoroaniline

Formula XVII

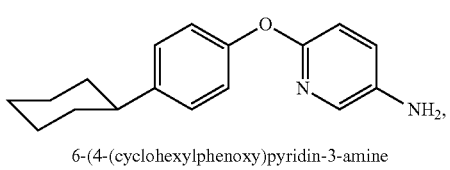

6-(4-cyclohexylphenoxy)pyridin-3-amine

Formula XVIII

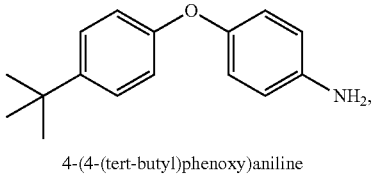

4-(4-(tert-butyl)phenoxy)aniline

Formula XIX

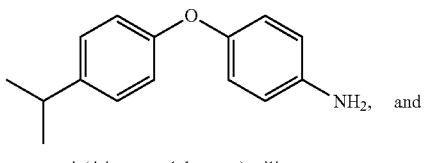

4-(4-isopropylphenoxy)aniline, and

Formula XX

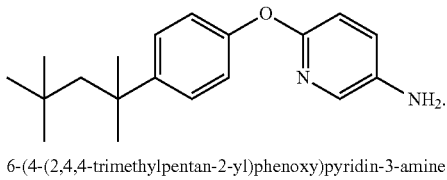

6-(4-(2,4,4-trimethylpentan-2-yl)phenoxy)pyridin-3-amine

In a particularly preferred embodiment, there is provided a process according to the second aspect of the invention or a hydrochloride salt according to the fourth aspect of the invention, wherein said compound of formula (I) is 6-(4-(tert-butyl)phenoxy)pyridin-3-amine, i.e. the hydrochloride salt obtained by the process according to the second aspect of the invention or the hydrochloride salt according to the fourth aspect of the invention is 6-(4-(tert-butyl)phenoxy)pyridin-3-amine hydrochloride.

In a further particularly preferred embodiment, there is provided a process according to the third aspect of the invention or a monohydrochloride salt according to the fifth aspect of the invention, wherein said compound of formula (I) is 6-(4-(tert-butyl)phenoxy)pyridin-3-amine, i.e. the monohydrochloride salt obtained by the process according to the third aspect of the invention or the monohydrochloride salt according to the fifth aspect of the invention is 6-(4-(tert-butyl)phenoxy)pyridin-3-amine monohydrochloride.

In a particularly preferred embodiment, there is provided a monohydrochloride salt according to the fifth aspect of the invention, wherein said monohydrochloride salt is 6-(4-(tert-butyl)phenoxy)pyridin-3-amine monohydrochloride and has a melting point of about 168° C. to about 178° C., preferably about 171° C. to about 175° C., most preferably about 173° C. (measured using differential scanning calorimetry (DSC)).

Figure 3:
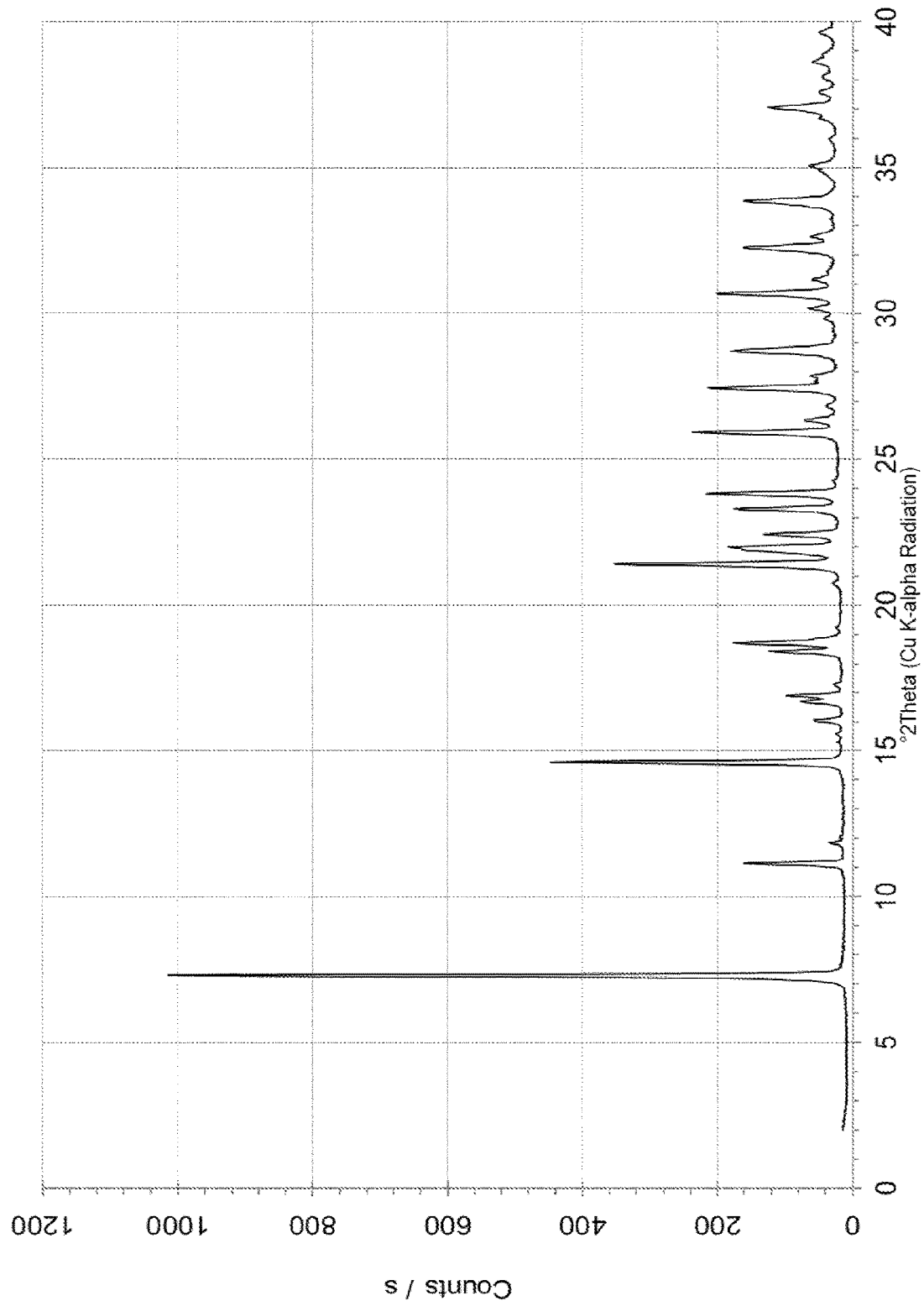
FIG. 3 shows an X-ray powder diffraction (XRPD) diffractogram of the monohydrochloride salt of the compound of formula (Ia), i.e. 6-(4-(tert-butyl)phenoxy)pyridin-3-amine monohydrochloride.
Figure 4:
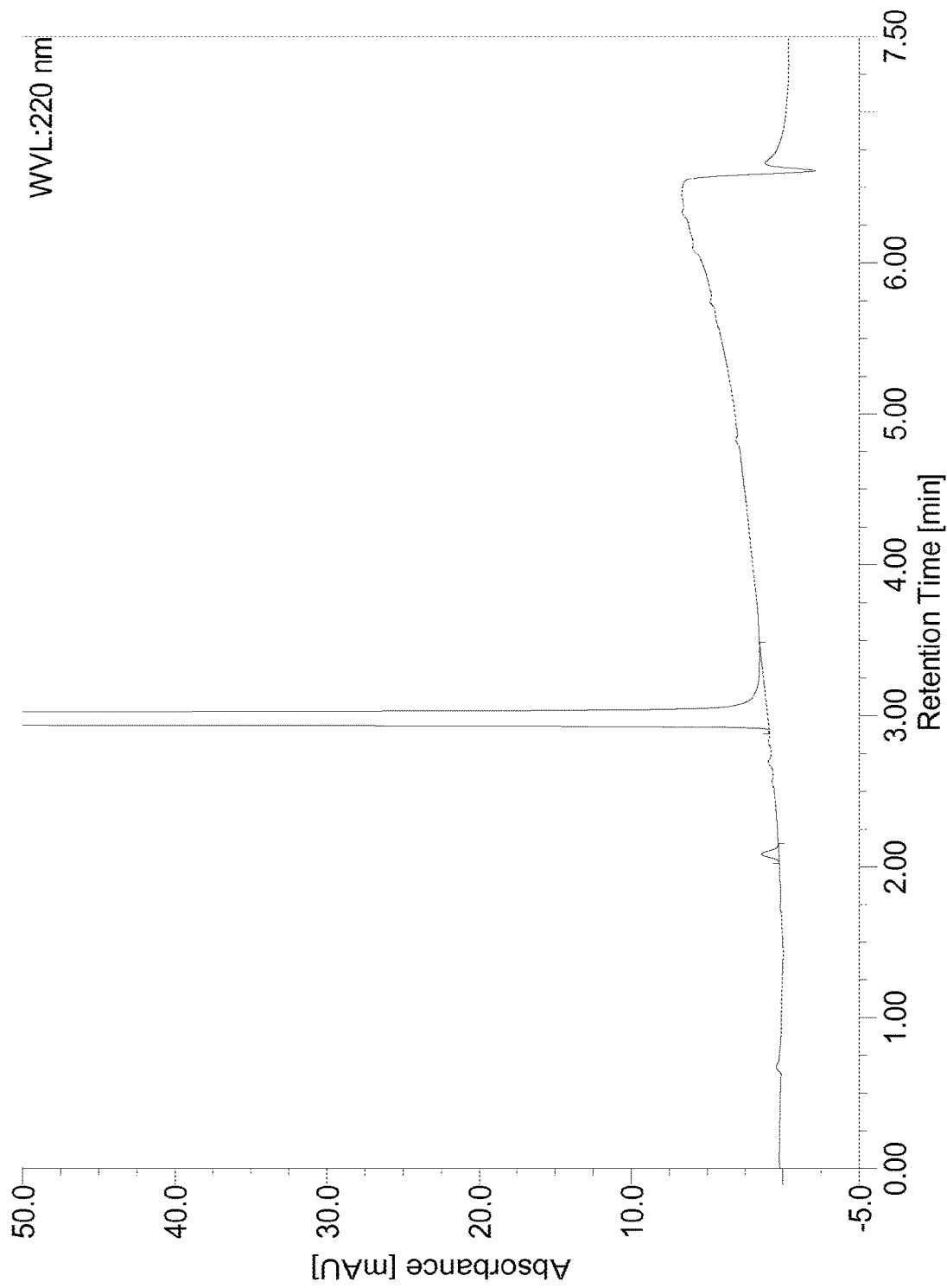
FIG. 4 shows an HPLC chromatogram of the compound of formula (Ia), i.e. 6-(4-(tert-butyl)phenoxy)pyridin-3-amine (purity: 99.9%), obtained by the process of the invention (see Example 3A).
Figure 5:
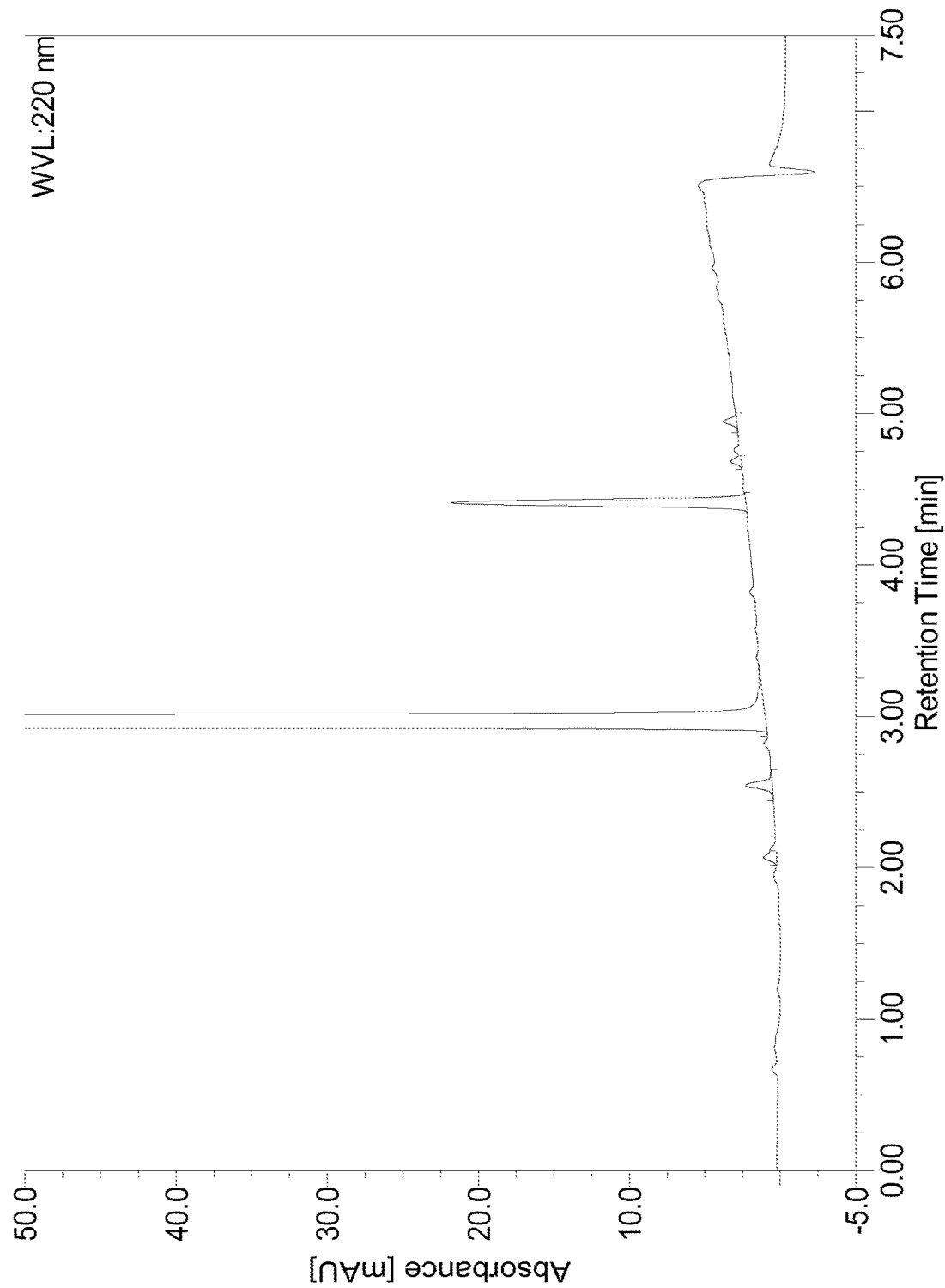
FIG. 5 shows a reference HPLC chromatogram of the compound of formula (Ia), i.e. 6-(4-(tert-butyl)phenoxy)pyridin-3-amine, obtained by the process described in WO2013/093885 (Example 2).

In a further particularly preferred embodiment, there is provided a monohydrochloride salt according to the fifth aspect of the invention, wherein said monohydrochloride salt is 6-(4-(tert-butyl)phenoxy)pyridin-3-amine monohydrochloride and has an X-ray powder diffraction pattern comprising 2θ values as shown in FIG. 3 measured using CuKα radiation.

In a preferred embodiment, there is provided a monohydrochloride salt according to the fifth aspect of the invention, wherein said monohydrochloride salt is 6-(4-(tert-butyl)phenoxy)pyridin-3-amine monohydrochloride and has a purity of 100% (>=95% area measured by HPLC-UV) after storage for 24 months at 25° C., 60% rh.

In a further preferred embodiment, there is provided a monohydrochloride salt according to the fifth aspect of the invention, wherein said monohydrochloride salt is 6-(4-(tert-butyl)phenoxy)pyridin-3-amine monohydrochloride and has a purity of 98.9% (>=95% area measured by HPLC-UV) after storage for 6 months at 40° C., 75% rh.

Use of the Hydrochloride and the Monohydrochloride Salts of the Invention

In a sixth aspect, the present invention provides a hydrochloride salt of the compound of formula (I) according to the fourth aspect of the invention and its embodiments described above, preferably 6-(4-(tert-butyl)phenoxy)pyridin-3-amine hydrochloride, for use as a medicament.

In a seventh aspect, the present invention provides a monohydrochloride salt of the compound of formula (I) according to the fifth aspect of the invention and its embodiments described above, preferably 6-(4-(tert-butyl)phenoxy)pyridin-3-amine monohydrochloride, for use as a medicament.

In an eights aspect, the present invention provides a hydrochloride salt of the compound of formula (I) according to the fourth aspect of the invention and its embodiments described above, preferably 6-(4-(tert-butyl)phenoxy)pyridin-3-amine hydrochloride, for use in a method of treatment and/or prevention of cancer.

Also provided is the use of a hydrochloride salt of the compound of formula (I) according to the fourth aspect of the invention and its embodiments described above, preferably 6-(4-(tert-butyl)phenoxy)pyridin-3-amine hydrochloride for the manufacture of a medicament for the treatment and/or prevention of cancer.

Also provided is the use of a hydrochloride salt of the compound of formula (I) according to the fourth aspect of the invention and its embodiments described above, preferably 6-(4-(tert-butyl)phenoxy)pyridin-3-amine hydrochloride for the treatment and/or prevention of cancer.

In a ninth aspect, the present invention provides a monohydrochloride salt of the compound of formula (I) according to the fifth aspect of the invention and its embodiments described above, preferably 6-(4-(tert-butyl)phenoxy)pyridin-3-amine monohydrochloride, for use in a method of treatment and/or prevention of cancer.

Also provided is the use of a monohydrochloride salt of the compound of formula (I) according to the fifth aspect of the invention and its embodiments described above, preferably 6-(4-(tert-butyl)phenoxy)pyridin-3-amine monohydrochloride for the manufacture of a medicament for the treatment and/or prevention of cancer.

Also provided is the use of a monohydrochloride salt of the compound of formula (I) according to the fifth aspect of the invention and its embodiments described above, preferably 6-(4-(tert-butyl)phenoxy)pyridin-3-amine monohydrochloride for the treatment and/or prevention of cancer.

In one embodiment of the fourth and fifth aspect of the invention, said cancer is a Notch dependent cancer, preferably a Notch dependent cancer selected from the group consisting of T cell-Acute lymphoblastic leukemia (T-ALL), chronic myeloid leukemia (CML), chronic lymphocytic leukemia (CLL), Mantle cell lymphoma (MCL), breast cancer, pancreatic cancer, prostate cancer, melanoma, brain tumors, tumor angiogenesis, and colorectal cancer.

EXAMPLES

Hereinafter, the present invention is described in more details and specifically with reference to the examples, which however are not intended to limit the present invention.

Materials:

4-(tert-butyl)-phenol (formula (IIIa)) and 2-chloro-5-nitro-pyridine (formula (IVa)) used for the exemplified embodiments of this invention are commercially available from various sources, e.g. may be purchased from Sigma-Aldrich. Generally, building blocks of formula (III) and (IV) are known and commercially available.

Compounds of formula (II) may be obtained according to general procedure A.

Compounds of formula (I) may be obtained according to general procedure B.

The monohydrochloride salts of the compounds of formula (I) described herein may be obtained according to general procedure C.

Instrumentation:
HPLC:
Device: Agilent 1100 series with DAD
Software: CDS Chromeleon 6.8
Column: Advanced Materials Technology Halo C18, 2.7 μm, 100 mm×4.6 mm
Column temperature: 20° C.
Mobile Phase A: Water
Mobile Phase B: Acetonitrile

|  | Time [min] | % A | % B |  |
|---|---|---|---|---|
| Gradient: | 0 | 50 | 50 |  |
|  | 5 | 0 | 100 |  |
|  | 5 | 50 | 50 |  |
|  | 7.5 | 50 | 50 | (Equilibration) |

Flow rate: 1.2 ml/min
Injection Volume: 2.0 μL
Sample solvent: Acetonnitrile for the compound of formula (Ia)
Acetonitrile/water 3:1 v/v for the monohydrochloride salt of the compound of formula (Ia)
Sample Concentration: 0.8 mg/mL
Autosampler temperature: 20° C.
Detection: UV at 220 nm
XRPD:
The X-ray powder diffraction studies were performed using a Bruker D8 Advance using a Cu anode at 40 kV, 40 mA. The software used for data collection was Diffrac. plus Part 11, Version 3. No background correction or smoothing was applied to the patterns.

General Procedure A: Coupling

A compound of formula (III) (1 equiv) and a compound of formula (IV) (1 equiv) are dissolved in DMF or in DMSO (5 vol) at room temperature (rt), followed by addition of $K_2CO_3$ (about 1.5 equiv). The mixture is stirred at rt until one or preferably both of the compounds of formula (III) and (IV) is fully converted, whereafter ethyl acetate (8 vol) and water (10 vol) are added. The layers are separated, the organic layer is washed with aqueous $NaHCO_3$ (4 vol) and brine (4 vol) and dried over anhydrous $Na_2SO_4$ (0.5-1% wt/wt). The suspension is filtered and the filter cake ($Na_2SO_4$) is washed with ethyl acetate (3 vol).

Optional Crystallization:
The combined filtrates are concentrated to about half their volume (i.e. ca. 6 vol ethyl acetate are distilled off). Subsequently, heptane (10 vol) is added at Tout=50° C. and part of the solvent (about 10 vol) is distilled off. The resulting concentrated solution is cooled to Tout=−20° C. to afford a suspension. The suspension is filtered and the filter cake is washed with cold heptane (4 vol) and dried on a rotary evaporator to afford the respective nitro-diaryl compound of formula (II).

General Procedure B: Hydrogenation

In an autoclave, a compound of formula (II) as obtainable according to general procedure A is dissolved in ethyl acetate (5 vol). Then, a suspension of palladium on activated charcoal (preferably having a Pd-content of 5% wt/wt; preferably about 1.25 mol % Pd) in ethyl acetate (1 vol) is added to the solution at rt via a funnel and the funnel is rinsed with ethyl acetate (3 vol). The autoclave is purged with hydrogen, then the suspension is stirred under a hydrogen pressure of 0.5 bar at rt until full conversion. Afterwards, the suspension is filtered and the filter cake is rinsed with ethyl acetate (3 vol).

Optional Workup Comprising Crystallization:
The filtrate is concentrated under reduced pressure to about half its volume. Then, activated charcoal is added at rt and the resulting suspension is stirred at rt. Subsequently, the suspension is filtered and the filter cake is washed with ethyl acetate (2×2 vol). The combined filtrates are concentrated under reduced pressure to about ⅓ of the initial volume and heptane (7 vol) is added at Tout=40° C., before distilling off about half of the solvent. The concentrated solution is cooled to Tout=−20° C. to afford a suspension which is further cooled to Tout=−24° C. Afterwards, the suspension is filtered and the filter cake is washed with cold heptane (3 vol) and dried on the filter overnight to afford the respective amino-diaryl compound of formula (I).

General Procedure C: Salt Formation

A compound of formula (I) is dissolved in 2-propanol (4 vol). The solution is heated to Tout=40° C. and 5-6 N HCl in 2-propanol (about 1.0 equiv) is added dropwise at Tout=40° C. ($Ti_{max}$=44.9° C.). Optionally, seeds of the monohydrochloride salt of the compound of formula (I) (0.1% wt/wt) are then added. The (seeded) mixture is stirred for about 0.5 h at Ti=40° C. to give a suspension. Heptane (4 vol) is added at Ti=40° C. and the suspension is further warmed to Ti=45° C. A second portion of heptane (8 vol) is added. Then the mixture is warmed to Tout=55° C. and kept stirring at this temperature for about 1 h.

Workup:
The suspension is cooled to Ti=13° C. over a period of about 16 h, followed by further cooling to Ti=0° C. over a period of about 30 min and stirring at Ti=0° C. for 1 h. Subsequently, the suspension is filtered and the filter cake is washed with a 10:1 mixture of heptane and 2-propanol (3 vol). The filter cake is dried on a rotary evaporator (Tout=50° C., <10 mbar) for 3 d to afford the monohydrochloride salt of the compound of formula (I), typically as a colourless, crystalline solid.

Example 1A: 2-(4-(tert-butyl)phenoxy)-5-nitropyridine (Formula (IIa))

According to general procedure A: 4-(tert-butyl)-phenol (formula (IIIa), 3.98 kg) and 2-chloro-5-nitro-pyridine (formula (IVa), 4.13 kg) were dissolved in DMSO (21 L) at room temperature (rt), followed by addition of $K_2CO_3$ (5.41 kg) over 17 min at rt. The mixture was stirred at rt for 17.25 h, whereafter ethyl acetate (33 L) and water (20 L) were added. The resulting biphasic mixture was stirred for 35 min and allowed to stand for another 35 min before the layers were separated. The organic layer was washed with aqueous $NaHCO_3$ (8% wt/wt, 16.5 L) and brine (16.5 L) and dried over anhydrous $Na_2SO_4$ (2.5 kg). The suspension was filtered and the filter cake ($Na_2SO_4$) was washed with ethyl acetate (13 L). Then, the combined filtrates were concentrated under reduced pressure (25 L ethyl acetate were distilled off). Subsequently, heptane (isomeric mixture, 41 L) was added at Tout=50° C. over 7 min and 42 L solvent were distilled off under reduced pressure. The resulting yellow solution was cooled to Tout=−20° C. over 20 h and stirred at that temperature for 65 min to afford a suspension. The suspension was filtered and the filter cake was washed with cold heptane (isomeric mixture, 16.5 L) and dried on a rotary evaporator overnight to afford 2-(4-(tert-butyl)phenoxy)-5-nitropyridine (Formula (IIa), 6.2 kg, 87%) as a white solid.

Example 1B: 2-(4-(tert-butyl)phenoxy)-5-nitropyridine (Formula (IIa))

According to general procedure A: 4-(tert-butyl)-phenol (formula (IIIa), 7.94 kg) and 2-chloro-5-nitro-pyridine (formula (Va), 8.36 kg) were dissolved in DMSO (42 L) at room temperature (rt), followed by addition of $K_2CO_3$ (10.96 kg) over 12 min at rt. The mixture was stirred at rt for 21.5 h, whereafter ethyl acetate (66 L) and water (42 L) were added. The resulting biphasic mixture was stirred for 68 min and allowed to stand for another 2 h before the layers were separated. The organic layer was washed with aqueous $NaHCO_3$ (8% wt/wt, 33 L) and brine (33 L) and dried over anhydrous $Na_2SO_4$ (5 kg). The suspension was filtered and the filter cake ($Na_2SO_4$) was washed with ethyl acetate (25 L). Then, the combined filtrates were concentrated under reduced pressure (48 L ethyl acetate were distilled off). Subsequently, heptane (isomeric mixture, 84 L) was added at Tout=50° C. over 67 min and 79 L solvent were distilled off under reduced pressure. The resulting yellow solution was cooled to Tout=-20° C. over 20 h and stirred at that temperature for 61 min to afford a suspension. The suspension was filtered and the filter cake was washed with cold heptane (isomeric mixture, 33 L) and dried on a rotary evaporator overnight to afford 2-(4-(tert-butyl)phenoxy)-5-nitropyridine (Formula (IIa), in two portions 4.96 and 5.06 kg, 70%) as a white solid. However, material coated in the vessel, dissolved with 20 L ethyl acetate combined with mother liquor was re-transferred into solvent switch from ethyl acetate to heptane according to general process leading to third portion of 3.59 kg (23%) as a white solid. Total overall yield increased to 93% in stage 1.

Example 2 (Comparative Example): 6-(4-(tert-butyl)phenoxy)pyridin-3-amine (Formula (Ia)) Obtained by the Process Described in WO2013/093885

2-(4-(tert-butyl)phenoxy)-5-nitropyridine (Formula (IIa), 8.6 g) and palladium on activated charcoal (2.35 g, 10% wt/wt palladium) in MeOH (86 mL) were stirred under a $H_2$-atmosphere (0.5 bar) at room temperature for 2 h to afford 6-(4-(tert-butyl)phenoxy)pyridin-3-amine (Formula (Ia)). However, N-methylated by-product was observed by HPLC and a Pd content of 6.9 ppm was detected by elemental analysis.

Example 3A: 6-(4-(tert-butyl)phenoxy)pyridin-3-amine (Formula (Ia))

According to general procedure B: In an autoclave, 2-(4-(tert-butyl)phenoxy)-5-nitropyridine (Formula (IIa), 1.2 kg) was dissolved in ethyl acetate (6 L). Then, a suspension of palladium on activated charcoal (119 g, 5% wt/wt palladium) in ethyl acetate (1.2 L) was added to the solution at rt via a funnel and the funnel was rinsed with ethyl acetate (3.6 L). The autoclave was purged with hydrogen (5 bar), then the suspension was stirred (832 rpm) under a hydrogen pressure of 0.5 bar at rt until full conversion (2 h 20 min). Afterwards, the suspension was filtered and the filter cake was rinsed with ethyl acetate (3.6 L).

Workup: In this campaign five shots of hydrogenation runs were combined and treated according to general process:

The filtrates (from five runs) were combined concentrated under reduced pressure (74 L ethyl acetate were distilled off). Then, activated charcoal (605 g) was added at Tout=25° C. and the resulting suspension was stirred at Tout=25° C. for 1 h 10 min. Subsequently, the suspension was filtered and the filter cake was washed with ethyl acetate (2×12 L). The combined filtrates were concentrated under reduced pressure (42 L ethyl acetate were distilled off) and heptane (isomeric mixture, 42 L) was added at Tout=40° C. over 12 min, before distilling off 36 L of solvent under reduced pressure. The concentrated solution was cooled to Tout=-20° C. over 6 h to afford a suspension which was further stirred for 1 h at Tout=-24° C. Afterwards, the suspension was filtered and the filter cake was washed with cold heptane (isomeric mixture, 19 L) and dried on the filter overnight to afford 6-(4-(tert-butyl)phenoxy)pyridin-3-amine (Formula (Ia), 4.95 kg, 91%) as a reddish solid.

Example 3B: 6-(4-(tert-butyl)phenoxy)pyridin-3-amine (Formula (Ia))

According to general procedure B: In an autoclave, 2-(4-(tert-butyl)phenoxy)-5-nitropyridine (Formula (IIa), 50 g) was dissolved in 2-propanol (0.4 L). Then, a suspension of palladium on activated charcoal (5 g, 5% wt/wt palladium) in 2-propanol (25 mL) was added to the solution at rt via a funnel and the funnel was rinsed with 2-propanol (25 mL). The autoclave was purged with hydrogen (5 bar), then the suspension was stirred (832 rpm) under a hydrogen pressure of 0.1 bar at rt until full conversion (7 h 30 min). Afterwards, the suspension was filtered and the filter cake was rinsed with 2-propanol (0.2 L).

Workup: The filtrate was concentrated under reduced pressure (0.65 L 2-propanol were distilled off) and 6-(4-(tert-butyl)phenoxy)pyridin-3-amine was isolated as a solid.

Example 4: 6-(4-(tert-butyl)phenoxy)pyridin-3-amine monohydrochloride

According to general procedure C: 6-(4-(tert-butyl)phenoxy)pyridin-3-amine (Formula (Ia), 4.95 kg), were dissolved in 2-propanol (20 L). The solution was heated to Tout=40° C. and 5-6 N HCl in 2-propanol (3.7 L, 1.01 equiv) was added dropwise over 20 min at Tout=40° C. ($Ti_{max}$=44.9° C.). Seeds of 6-(4-(tert-butyl)phenoxy)pyridin-3-amine monohydrochloride (5 g) were added and the seeded mixture was stirred for 0.5 h at Ti=40° C. to give a suspension. Heptane (isomeric mixture, 20 L) was added over a period of 33 min at Ti=40° C. and the suspension was further warmed to Ti=45° C. A second portion of heptane was added (isomeric mixture, 40 L) was added dropwise over 54 min. Then the mixture was warmed to Tout=55° C. and kept stirring at this temperature for 1 h.

Workup:

The suspension was cooled to Ti=13° C. over a period of 16 h, followed by further cooling to Ti=0° C. over a period of 30 min and stirring at Ti=0° C. for 1 h. Subsequently, the suspension was filtered and the filter cake was washed with a 10:1 mixture of heptane (isomeric mixture) and 2-propanol (2×16.5 L). The filter cake was dried on a rotary evaporator (Tout=50° C., <10 mbar) for 3 d to afford the title compound as a colourless, crystalline solid (5.02 kg, 88%).

Example 5: Salt formation with 6-(4-(tert-butyl)phenoxy)pyridin-3-amine

Formation of different salts were tested according to the procedure indicated in Table 1 below:

TABLE 1

Salt formation with 6-(4-(tert-butyl)phenoxy)pyridin-3-amine

| Acid | Eq. acid used | procedure | comments |
|---|---|---|---|
| HCl as 5-6N HCl in 2-PrOH | 1 eq (later using 1.01 eq.) | According to general procedure C | Established process |
| HCl as 1.25M HCl in 2-PrOH | 2.5 eq | According to 1 eq. process, however, product turned out to be mixed HCl | DSC revealed unspecified mixture of Mono and Di-HCl salt |
| maleic acid | 1 eq. | 4.13 g dissolved in 10 vol EtOH, at 50° C. added 1 eq. maleic acid to give solution; cooled down to 0° C., however, still solution obtained | Reaction discarded |
| fumaric acid | 1 eq. | 4.13 g dissolved in 10 vol EtOH, at 50° C. added 1 eq. fumaric acid to give solution; cooled down to 0° C., however, still solution obtained | Reaction discarded |
| benzoic acid | 1 eq. | 4.13 g dissolved in 8 vol EtOH suspended, at 50° C. added 1 eq. benzoic acid to give solution; cooled down to 0° C., however, still solution obtained | Reaction discarded |
| tartaric acid | 0.5 eq. | 4.13 g dissolved in 8 vol EtOH suspended, at 50° C. added 0.5 eq. tartaric acid to give very fine white solid; which did not give a thicker suspension, even at rt upon cooling | Reaction discarded |
| tartaric acid | 1 eq. | 4.13 g dissolved in 8 vol EtOH suspended, at 50° C. added 1 eq. tartaric acid to give solution, which did not give a suspension even at rt upon cooling | Reaction discarded |

Example 6: Forced degradation of 6-(4-(tert-butyl)phenoxy)pyridin-3-amine monohydrochloride Instrumentation:
Light stability chamber: Solarbox 1500e
Oven: Salvis Vacuum drying oven VC-20
Heating unit: Ikamag RET-GS with IKA ETS SD and stainless steel heating block
Vials: Supelco V-Vials and screw caps with PTFE septa
Gas tight vials: Agilent 10 mL HS-GC clear glass vials and crimp caps with Not applicable PTFE septa
Quartz glass cuvette: Hellma precision cuvette Suprasil, Type 117.100-QS, 10 mm path length, screw capped with silicone septa
HPLC: As described above
Analytical Methods:
The HPLC test method described above was used to determine the assay and purity of 6-(4-(tert-butyl)phenoxy)pyridin-3-amine monohydrochloride before the forced degradation experiments and the area % content of individual impurities and degradation products in the 6-(4-(tert-butyl)phenoxy)pyridin-3-amine monohydrochloride samples obtained from the degradation experiments.

Identity of 6-(4-(tert-butyl)phenoxy)pyridin-3-amine monohydrochloride was determined by comparison of the retention time against a reference.

The assay and the purity of 6-(4-(tert-butyl)phenoxy)pyridin-3-amine monohydrochloride were determined using HPLC with UV detection at 220 nm utilizing the area normalization methodology for purity determination and external standard calibration for assay determination. During all experiments the UV spectra from 200 nm to 950 nm have been recorded and also the peak purity of 6-(4-(tert-butyl)phenoxy)pyridin-3-amine monohydrochloride was assessed.

Only single determinations for each test condition had been performed.

For each test condition described below, one sample was prepared and analyzed in accordance with the HPLC method.

1. Solid State with Thermal Stress

Approximately 20.4 mg and 50.1 mg of 6-(4-(tert-butyl)phenoxy)pyridin-3-amine monohydrochloride were weighed into a Supelco V-Vial. The vial was closed with the screw cap and stored in the heating block of the heating unit operated at 100° C.±5° C. for 20 h (20 mg sample) and 68 h (50 mg sample), respectively.

After storage at 100° C. for the intended time each sample was cooled down to room temperature and the content of the vial was dissolved in about 4 mL of the sample solvent (acetonitrile/water 3:1 v/v). The obtained solution was quantitatively transferred into a 25 mL volumetric flask (20 mg sample), or to a 50 mL volumetric flask (50 mg sample), respectively. Then the vial was rinsed three times with about 4 mL sample solvent, whereupon each time the content of the vial was also transferred into the 25 mL volumetric flask. After the flask was filled up to volume with the sample solvent and was shaken well, an aliquot of this solution was transferred into a HPLC vial for analysis.

Results: 6-(4-(tert-butyl)phenoxy)pyridin-3-amine monohydrochloride is stable in solid state at 100° C. No significant changes were observed in the purity and the purity profile after 68 h storage at 100° C. The observed decrease in the assay was within the accepted variability of the method (±2%).

2. Solid State Stressed by UV/VIS Radiation

Two samples of 20.23 mg and 20.17 mg of 6-(4-(tert-butyl)phenoxy)pyridin-3-amine monohydrochloride were weighed each into a quartz glass cuvette. Both cuvettes were closed with the screw cap. One of the cuvettes was protected by wrapping it in aluminium foil. This sample served as dark control. Both cuvettes were placed alongside each other in the light stability chamber and were then exposed in accordance to guideline [4] to UV/VIS radiation applying energy of 500 W/m$^2$ until a total illumination of 1200 kLux·h was reached. After exposure to the UV/VIS radiation for an illumination of 1200 kLux·h the sample was brought to room temperature and the content of the cuvette was dissolved in about 2 mL of the sample solvent (acetonitrile/water 3:1 v/v). The obtained solution was quantitatively transferred into a 25 mL volumetric flask. Then the cuvette was rinsed five times with about 2 mL sample solvent, whereupon each time the content of the cuvette was also transferred into the 25 mL volumetric flask. After the flask was filled up to volume with the sample solvent and was shaken well, an aliquot of this solution was transferred into a HPLC vial for analysis. Result: In solid state 6-(4-(tert-butyl)phenoxy) pyridin-3-amine monohydrochloride is stable against UV/VIS radiation. After an illumination of 1200 kLux·h, applying an energy of 500 W/m$^2$, the purity decreased by 0.6 area % which was mainly related to the occurrence of two unknown impurities. The observed decrease in the assay of 2.1% w/w was not related to the UV/VIS radiation, as the assay of the dark control had a similar value (decrease by 2.4% w/w).

3. Alkaline and Thermal Stress in Aqueous Solution

Approximately 20 mg (4×) of 6-(4-(tert-butyl)phenoxy) pyridin-3-amine monohydrochloride were weighed into a 10 mL GC-HS vial and 2.0 mL of 0.1 M aqueous NaOH were added. The four vials were crimped and shaken. Two of the vials were stored in an oven operated at 60° C.±5° C. and two in an oven operated at 90° C.±5° C. In addition, a blank sample was prepared by transferring a volume of 2.0 mL of 0.1 M aqueous NaOH into a 10 mL GC-HS vial. After crimping, the vial containing the blank was stored in the oven operated at 90° C.±5° C. The test conditions are summarized in Table 2:

TABLE 2

Test conditions of alkaline and thermal stress in aqueous solution

| Sample weight | Concentration | Test condition | Storage time |
| --- | --- | --- | --- |
| 0 | 0 mg/mL | 0.1 M NaOH/90° C. | 66 h |
| 20.37 mg | 10.2 mg/mL | 0.1 M NaOH/60° C. | 18 h |
| 20.63 mg | 10.3 mg/mL | 0.1 M NaOH/60° C. | 66 h |
| 20.32 mg | 10.2 mg/mL | 0.1 M NaOH/90° C. | 18 h |
| 20.78 mg | 10.4 mg/mL | 0.1 M NaOH/90° C. | 66 h |

After storage at the defined conditions for the intended time each sample was cooled down to room temperature. Then, the samples were neutralized by adding 2.0 mL of an aqueous 0.1 M HCl solution. For each sample the vial content was quantitatively transferred into a 25 mL volumetric flask. Then the vial was rinsed three times with about 5 mL sample solvent (acetonitrile/water 3:1 v/v), whereupon each time the content of the vial was also transferred into the 25 mL volumetric flask. After the flask was filled up to volume with the sample solvent and was shaken well, an aliquot of this solution was transferred into a HPLC vial for analysis.

All recorded chromatograms were evaluated for identity, assay and purity according to the analytical method [1]. In addition, peak purity was assessed in the chromatograms of the stability samples. For each analytical sequence a SST was performed as specified in the analytical method [1]. All SST criteria were fulfilled for each of the analytical sequences.

Example 7: Solubility of 6-(4-(tert-butyl)phenoxy) pyridin-3-amine monohydrochloride vs. 6-(4-(tert-butyl)phenoxy)pyridin-3-amine The solubilities in water of 6-(4-(tert-butyl)phenoxy)pyridin-3-amine (formula (Ia)) and the monohydrochloride salt thereof, i.e. 6-(4-(tert-butyl)phenoxy)pyridin-3-amine monohydrochloride, were assessed at various pH-values according to Tables 3 and 4. The solubility in water of 6-(4-(tert-butyl)phenoxy)pyridin-3-amine (formula (Ia)) according to Table 3 was assayed as follows: Free base 500 mg were charged into 14 mL of acidic media at pH=2, 4, at neutral pH=7 and basic pH=10 to afford suspensions within calculated concentration of appr. 35 mg/mL. The solubility in water of 6-(4-(tert-butyl)phenoxy)pyridin-3-amine monohydrochloride according to Table 4 was assayed as follows: HCl salt 100 mg each were charged into acidic media at pH=2 and 4 and neutral media pH=7 to furnish solutions. Most important observation was to that at a neutral solution at pH=7 drops down to pH=1 by charging HCl salt 100 mg.

It was found that 6-(4-(tert-butyl)phenoxy)pyridin-3-amine (formula (Ia)) is very poorly soluble in water, irrespective of the pH. The solubility limit of the compound of formula (Ia) in 0.01% HCl was determined to be 100 mg in 190 mL (0.53 mg/mL). In contrast, the monohydrochloride salt of the compound of formula (Ia) was found to be well-soluble in water.

TABLE 3

Solubility of 6-(4-(tert-butyl)phenoxy)pyridin-3-amine at different pH-values

| solvent | PH solvent | mass in mg | volume in mL | conc. in mg/mL | soluble | pH solution |
| --- | --- | --- | --- | --- | --- | --- |
| 15% acetic acid soln. | 2 | 500 | 14 ml | 33.33 | no | 2 |
| Fluka 33643 (pH = 4) | 4 | 500 | 14 ml | 33.33 | no | 4 |
| Fluka 33646 (PH = 7) | 7 | 500 | 14 ml | 33.33 | no | 7 |
| Fluka 33649 (pH = 10) | 10 | 500 | 14 ml | 33.33 | no | 10 |

TABLE 4

HCl salt of 6-(4-(tert-butyl)phenoxy)pyridin-
3-amine solubilities at different pH-values

| solvent | pH solvent | mass in mg | volume in mL | conc. in mg/mL | soluble | pH solution |
|---|---|---|---|---|---|---|
| 15% acetic acid soln. | 2 | 100 | 0.6 ml | 166.66 | yes | |
| Fluka 33643 (pH = 4) | 4 | 100 | 1.4 ml | 71.43 | yes | 1 |
| Fluka 33646 (pH = 7) | 7 | 100 | 1.0 ml | 100.00 | yes | 1 |

Example 8: Stability studies of
6-(4-(tert-butyl)phenoxy)pyridin-3-amine
monohydrochloride For 6-(4-(tert-butyl)phenoxy)pyridin-3-amine monohydrochloride two different types of stability studies were performed including short-term and long-term stability studies, respectively, at 25° C. (RH, 60%), −5° C. and −20° C. for 36 months and an accelerated study at 40° C. (RH, 75%) over 6 months. The results of these studies are shown in tables 7-14 below. In terms of analytical determinations six tests were involved including appearance, assay free base mean and purity mean, water, IR and XRPD. Appearance was determined by visual inspection. The product should be a white or off-white powder. Water content was determined according to USP <921> coulometric method. Identification of 6-(4-(tert-butyl)phenoxy)pyridin-3-amine monohydrochloride by IR spectroscopy was done according to USP <197>, comparing the spectrum obtained to that of the reference standard. X-Ray powder diffraction (XRPD) was performed according to USP <941> against the reference XRPD spectrum. Purity and assay of free base was done by HPLC-UV. Two methods were used. Mobile phases in the first method were water and acetonitrile. Mobile phases in the second method were water (0.5 mL of trifluoroacetic acid was added to 1000 mL of water) and acetonitrile (0.4 mL of trifluoroacetic acid was added to 1000 mL of acetonitrile). Equipment and chromatographic conditions for identification and determination of purity and assay of the 6-(4-(tert-butyl)phenoxy)pyridin-3-amine monohydrochloride by HPLC-UV according to the first method and the second method, respectively, are shown in Tables 5 and 6.

TABLE 5

Equipment and chromatographic conditions
for identification and determination of
purity and assay of 6-(4-(tert-butyl)
phenoxy)pyridin-3-amine monohydrochloride
by HPLC-UV according to the first method

| | |
|---|---|
| HPLC model | Agilent 1100/1200 series |
| Detector | Diode Array Detector (DAD) |
| Column | Halo C18, 2.7 μm, 100 mm × 4.6 mm column |
| Gradient | Time : |
| | 0 min. |
| | 5.0 min. |
| | 10.0 min. |
| | 10.0 min. |
| | 12.5 min. |
| | Mobile phase A: |
| | 50% |
| | 0% |
| | 0% |
| | 50% |
| | 50% |
| | Mobile phase B: |
| | 50% |
| | 100% |
| | 100% |
| | 50% |
| | 50% |
| Flow rate | 1.2 mL/min |
| Autosampler temperature | 20° C. |
| Column temperature | 20° C. |
| Injection volume | 2 μl |
| Detection | 220 nm/UV |
| Slit width | 4 nm |
| Bandwidth | 4 nm |
| Reference wavelength | Off |
| Peak width | 0.10 min |
| Step | 0.01 sec |
| Acquisition time | 11 min |
| Run time | 15 min |

TABLE 6

Equipment and chromatographic conditions
for identification and determination of
purity and assay of the 6-(4-(tert-butyl)
phenoxy)pyridin-3-amine monohydrochloride
by HPLC-UV according to the second method

| | |
|---|---|
| HPLC model | Agilent 1100/1200 series |
| Detector | Diode Array Detector (DAD) |
| Column | Halo C18, 2.7 μm, 100 mm × 4.6 mm column |
| Gradient | Time : |
| | 0 min. |
| | 1.0 min. |
| | 5.0 min. |
| | 8.0 min. |
| | 11.0 min. |
| | 11.1 min. |
| | 15.0 min. |
| | Mobile phase A: |
| | 60% |
| | 60% |
| | 30% |
| | 10% |
| | 10% |
| | 60% |
| | 60% |
| | Mobile phase B: |
| | 40% |
| | 40% |
| | 70% |
| | 90% |
| | 90% |
| | 40% |
| | 40% |
| Flow rate | 0.8 mL/min |
| Autosampler temperature | 20° C. |
| Column temperature | 30° C. |
| Injection volume | 3 μl |
| Detection | 220 nm/UV |
| Slit width | 2 nm |
| Bandwidth | 4 nm |
| Reference wavelength | Off |
| Peak width | 0.05 min |
| Step | 0.05 sec |
| Acquisition time | 11 min |
| Run time | 15 min |

TABLE 7

6 months stability studies with storage conditions: 25° C., 60% rh

|  | Release data | 3 mths | 6 mths |
|---|---|---|---|
| Acceptance Criteria | Result | Result | Result |
| White to off-white powder | White powder | White powder | White powder |
| 80.9-92.9% m/m (anhydrous, solvent free) | 87.0 | 88.8 | 87.2 |
| >= 95% area | 99.2 | 99.5 | 98.8 |
| Report results [% m/m] | 0.02 | 0.01 | 0.01 |
| Conforms to reference | complies | complies | complies |
| Conforms to reference | according to diffractogram | not tested | not tested |

TABLE 8

36 months stability studies with storage conditions: 25° C., 60% rh

|  | Release data | 3 mths | 6 mths | 9 mths | 12 mths | 18 mths | 24 mths | 36 mths |
|---|---|---|---|---|---|---|---|---|
| Acceptance Criteria | Result | Result | Result | Result | Result | Result | Result | Result |
| White to off-white powder | White powder | White powder | White powder | White powder | White powder | White powder | White powder | Pending |
| 80.9-92.9% m/m (anhydrous, solvent free) | not tested | not tested | 88.6 | 88.0 | 86.9 | 87.7 | 87.6 | Pending |
| >=95% area |  | not tested | 100.0 | 100.0 | 100.0 | 100.0 | 100.0 | Pending |
| Report results [% m/m] | 0.02 | 0.01 | 0.01 | 0.02 | 0.02 | 0.02 | 0.02 | Pending |
| Conforms to reference | Complies | Complies | Complies | Complies | Complies | Complies | Complies | Pending |
| Conforms to reference | according to diffracttogram | not tested | not tested | not tested | Complies | not tested | according to diffracttogram | Pending |

TABLE 9

6 months stability studies with storage conditions: 5° C.

|  | Release data | 3 mths | 6 mths |
|---|---|---|---|
| Acceptance Criteria | Result | Result | Result |
| White to off-white powder | White powder | White powder | White powder |
| 80.9-92.9% m/m (anhydrous, solvent free) | 89.4 | 87.2 | 87.6 |
| >= 95% area | 100.0 | 99 | 99 |
| Report results [% m/m] | 0.01 | 0.02 | 0.02 |
| Conforms to reference | complies | complies | complies |
| Conforms to reference | according to diffract-togram | not tested | not tested |

TABLE 10

36 months stability studies with storage conditions: 5° C.

|  | Release data | 3 mths | 6 mths | 9 mths | 12 mths | 18 mths | 24 mths | 36 mths |
|---|---|---|---|---|---|---|---|---|
| Acceptance Criteria | Result | Result | Result | Result | Result | Result | Result | Result |
| White to off-white powder | White powder | White powder | White powder | White powder | White powder | White powder | White powder | Pending |

TABLE 10-continued 36 months stability studies with storage conditions: 5° C.

| | Release data | 3 mths | 6 mths | 9 mths | 12 mths | 18 mths | 24 mths | 36 mths |
|---|---|---|---|---|---|---|---|---|
| 80.9-92.9% m/m (anhydrous, solvent free) | not tested | not tested | 87.5 | 89.6 | 87.3 | 87.0 | 88.3 | Pending |
| >=95% area | not tested | not tested | 100.0 | 100.0 | 100.0 | 100.0 | 100.0 | Pending |
| Report results [% m/m] | 0.01 | 0.02 | 0.02 | 0.03 | 0.02 | 0.01 | 0.02 | Pending |
| Conforms to reference | complies | Complies | Complies | Complies | Complies | Complies | Complies | Pending |
| Conforms to reference | according to diffracttogram | not tested | not tested | not tested | see diffractogram | not tested | according to diffracttogram | Pending |

TABLE 11

6 months stability studies with storage conditions: −20° C.

| | Release data | 3 mths | 6 mths |
|---|---|---|---|
| Acceptance Criteria | Result | Result | Result |
| White to off-white powder | White powder | White powder | White powder |
| 80.9-92.9% m/m (anhydrous, solvent free) | 89.4 | 86.1 | 87.3 |
| >= 95% area | 100.0 | 99 | 99 |
| Report results [% m/m] | 0.01 | 0.02 | 0.02 |
| Conforms to reference | complies | complies | complies |
| Conforms to reference | according to diffracttogram | not tested | not tested |

TABLE 12

36 months stability studies with storage conditions: −20° C.

| | Release data | 3 mths | 6 mths | 9 mths | 12 mths | 18 mths | 24 mths | 36 mths |
|---|---|---|---|---|---|---|---|---|
| Acceptance Criteria | Result | Result | Result | Result | Result | Result | Result | Result |
| White to off-white powder | White powder | White powder | White powder | White powder | White powder | White powder | pending | Pending |
| 80.9-92.9% m/m (anhydrous, solvent free) | not tested | not tested | 87.4 | 88.6 | 87.5 | 87.4 | 87.4 | Pending |
| >=95% area | not tested | not tested | 100.0 | 100.0 | 100.0 | 100.0 | 100.0 | Pending |
| Report results [% m/m] | 0.01 | 0.02 | 0.02 | 0.03 | 0.02 | 0.01 | 0.02 | Pending |
| Conforms to reference | Complies | Complies | Complies | Complies | Complies | Complies | Complies | Pending |
| Conforms to reference | according to diffracttogram | not tested | not tested | not tested | see diffractogram | not tested | according-to diffracttogram | Pending |

TABLE 13

6 months stability studies with storage conditions: 40° C., 75% rh

| | Release data | 3 mths | 6 mths |
|---|---|---|---|
| Acceptance Criteria | Result | Result | Result |
| White to off-white powder | White powder | White powder | White powder |
| 80.9-92.9% m/m (anhydrous, solvent free) | 87.0 | 89.2 | 87.4 |
| >= 95% area | 99.2 | 99.6 | 98.9 |
| Report results [% m/m] | 0.02 | 0.01 | 0.02 |
| Conforms to reference | complies | complies | complies |
| Conforms to reference | accor-ding to diffract-togram | not tested | complies |

TABLE 14

Summary of stability studies performed

| Test | Appearance | Assay free base, mean | Purity, mean | Water | IR | XRPD |
|---|---|---|---|---|---|---|
| Acceptance Criteria | White to off-white powder | 80.9-92.9% m/m (anhydrous, solvent free) | >=95% area | Report Results [% m/m] | Conforms to reference | Conforms to reference |
| Release data | 25° C., 60% rh +5° C. -20° C. +40° C., 75% rh | 25° C., 60% rh +5° C. -20° C. +40° C., 75% rh | 25° C., 60% rh +5° C. -20° C. +40° C., 75% rh | 25° C., 60% rh +5° C. -20° C. +40° C., 75% rh | 25° C., 60% rh +5° C. -20° C. +40° C., 75% rh | 25° C., 60% rh +5° C. -20° C. +40° C., 75% rh |
| 3 months | 25° C., 60% rh +5° C. -20° C. +40° C., 75% rh | 25° C., 60% rh +5° C. -20° C. +40° C., 75% rh | 25° C., 60% rh +5° C. -20° C. +40° C., 75% rh | 25° C., 60% rh +5° C. -20° C. +40° C., 75% rh | 25° C., 60% rh +5° C. -20° C. +40° C., 75% rh | 25° C., 60% rh +5° C. -20° C. +40° C., 75% rh |
| 6 months | 25° C., 60% rh +5° C. -20° C. +40° C., 75% rh | 25° C., 60% rh +5° C. -20° C. +40° C., 75% rh | 25° C., 60% rh +5° C. -20° C. +40° C., 75% rh | 25° C., 60% rh +5° C. -20° C. +40° C., 75% rh | 25° C., 60% rh +5° C. -20° C. +40° C., 75% rh | 25° C., 60% rh +5° C. -20° C. +40° C., 75% rh |
| 9 months | 25° C., 60% rh +5° C. -20° C. | 25° C., 60% rh +5° C. -20° C. | 25° C., 60% rh +5° C. -20° C. | 25° C., 60% rh +5° C. -20° C. | 25° C., 60% rh +5° C. -20° C. | 25° C., 60% rh +5° C. -20° C. |
| 12 months | 25° C., 60% rh +5° C. -20° C. | 25° C., 60% rh +5° C. -20° C. | 25° C., 60% rh +5° C. -20° C. | 25° C., 60% rh +5° C. -20° C. | 25° C., 60% rh +5° C. -20° C. | 25° C., 60% rh +5° C. -20° C. |
| 18 months | 25° C., 60% rh +5° C. -20° C. | 25° C., 60% rh +5° C. -20° C. | 25° C., 60% rh +5° C. -20° C. | 25° C., 60% rh +5° C. -20° C. | 25° C., 60% rh +5° C. -20° C. | 25° C., 60% rh +5° C. -20° C. |
| 24 months | 25° C., 60% rh +5° C. -20° C. | 25° C., 60% rh +5° C. -20° C. | 25° C., 60% rh +5° C. -20° C. | 25° C., 60% rh +5° C. -20° C. | 25° C., 60% rh +5° C. -20° C. | 25° C., 60% rh +5° C. -20° C. |
| 36 months (data pending) | 25° C., 60% rh +5° C. -20° C. | 25° C., 60% rh +5° C. -20° C. | 25° C., 60% rh +5° C. -20° C. | 25° C., 60% rh +5° C. -20° C. | 25° C., 60% rh +5° C. -20° C. | 25° C., 60% rh +5° C. -20° C. |

The invention claimed is:
1. A monohydrochloride salt of the compound of formula (I)

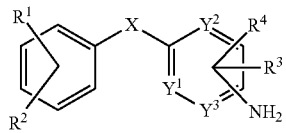

Formula (I)

wherein X is selected from O and NH; and wherein Y¹, Y² and Y³ are each independently selected from N and CH; and wherein R¹ and R² are each independently selected from H, C1-C10 alkyl and C3-C12 cycloalkyl and wherein R³ and R⁴ are each independently selected from H, halogen and C1-C10 alkyl.

2. The monohydrochloride salt of claim 1, wherein the compound has formula (Ia)

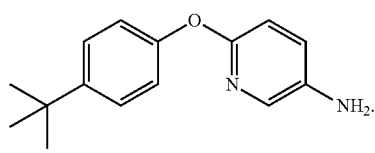

Formula (Ia)

3. The monohydrochloride salt of claim 2, wherein the salt is anhydrous.

4. The monohydrochloride salt of claim 2, characterized by having a melting point with an onset of 170.9° C. and peaking at 173.4° C.

5. The monohydrochloride salt of claim 2, characterized by having a melting point of 173° C.

6. The monohydrochloride salt of claim 2, characterized by differential scanning calorimetry (DSC) pattern substantially as set forth in FIG. 1.

7. The monohydrochloride salt of claim 2, having a purity of 99.9% pure as determined by HPLC.

8. The monohydrochloride salt of claim 2, wherein the salt is in a crystalline form.

9. The monohydrochloride salt of claim 8, characterized by an X-ray powder diffraction (XRPD) pattern substantially as set forth in FIG. 3.

10. The monohydrochloride salt of claim 8, characterized by having an X-ray powder diffractogram which has one or more peaks chosen from peaks (° 2θ) as set forth in FIG. 3, wherein the one or more peaks have a Cps intensity greater than 100.

11. The monohydrochloride salt of claim 8, wherein the one or more peaks (° 2θ) have a Cps intensity greater than 100 are selected from about 7.3°, about 14.6°, about 21.4°, about 27.4°, about 25.9°, about 30.7°, about 22.0°, about 33.8°, about 23.3°, about 23.8° and about 28.7°.

12. The monohydrochloride salt of claim 1, wherein the compound has formula (Ia)

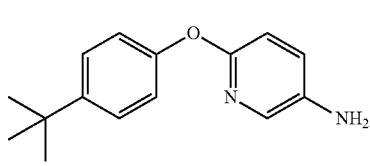

Formula (Ia)

wherein the monohydrochloride salt is characterized by having an X-ray powder diffractogram which has one or more peaks chosen from peaks (° 2θ) at 7.3° ±0.2°, 11.1° ±0.2°, 14.6° ±0.2°, 18.7° ±0.2°, 21.4° ±0.2°, 23.3° ±0.2°, 23.8° ±0.2°, 25.9° ±0.2°, 27.4° ±0.2°, and 30.7° ±0.2°.

13. The monohydrochloride salt of claim 12, wherein the salt is anhydrous.

14. The monohydrochloride salt of claim 12, characterized by having a melting point with an onset of 170.9° C. and peaking at 173.4° C.

15. The monohydrochloride salt of claim 12, characterized by having a melting point of 173° C.

16. The monohydrochloride salt of claim 12, characterized by differential scanning calorimetry (DSC) pattern substantially as set forth in FIG. 1.

17. The monohydrochloride salt of claim 12, having a purity of 99.9% pure as determined by HPLC.

18. The monohydrochloride salt of claim 12, wherein the salt is in a crystalline form.

19. The monohydrochloride salt of claim 18, characterized by an X-ray powder diffraction (XRPD) pattern substantially as set forth in FIG. 3.

20. The monohydrochloride salt of claim 18, characterized by having an X-ray powder diffractogram which has one or more peaks chosen from peaks (° 2θ) as set forth in FIG. 3, wherein the one or more peaks have a Cps intensity greater than 100.

21. The monohydrochloride salt of claim 18, wherein the one or more peaks (° 2θ) have a Cps intensity greater than 100 are selected from about 7.3°, about 14.6°, about 21.4°, about 27.4°, about 25.9°, about 30.7°, about 22.0°, about 33.8°, about 23.3°, about 23.8° and about 28.7°.

22. A pharmaceutical formulation comprising the monohydrochloride salt of claim 2 and an excipient.

* * * * *